(12) United States Patent
Wawrousek et al.

(10) Patent No.: US 10,376,837 B2
(45) Date of Patent: Aug. 13, 2019

(54) CONVERSION OF CARBON DIOXIDE UTILIZING CHEMOAUTOTROPHIC MICROORGANISMS SYSTEMS AND METHODS

(71) Applicant: The University of Wyoming Research Corporation, Laramie, WY (US)

(72) Inventors: Karen E. Wawrousek, Laramie, WY (US); Patrick Richards, Seattle, WA (US); Tengyan Zhang, Bellevue, WA (US); Alan E. Bland, Laramie, WY (US)

(73) Assignee: The University of Wyoming Research Corporation, Laramie, WY (US)

( * ) Notice: Subject to any disclaimer, the term of this patent is extended or adjusted under 35 U.S.C. 154(b) by 276 days.

(21) Appl. No.: 14/776,611

(22) PCT Filed: Mar. 14, 2014

(86) PCT No.: PCT/US2014/029843
§ 371 (c)(1),
(2) Date: Sep. 14, 2015

(87) PCT Pub. No.: WO2014/200598
PCT Pub. Date: Dec. 18, 2014

(65) Prior Publication Data
US 2016/0030884 A1    Feb. 4, 2016

Related U.S. Application Data

(60) Provisional application No. 61/782,762, filed on Mar. 14, 2013.

(51) Int. Cl.
*C12N 1/20*       (2006.01)
*B01D 53/84*     (2006.01)
(Continued)

(52) U.S. Cl.
CPC ............. *B01D 53/84* (2013.01); *B01D 53/62* (2013.01); *C12M 21/02* (2013.01); *C12M 43/06* (2013.01);
(Continued)

(58) Field of Classification Search
None
See application file for complete search history.

(56) References Cited

U.S. PATENT DOCUMENTS

| 3,325,537 A | 6/1967 | Beasley, Jr. et al. |
| 4,516,980 A | 5/1985 | Wheelock |

(Continued)

FOREIGN PATENT DOCUMENTS

| AU | 2014278749 | 3/2018 |
| AU | 2014236594 | 6/2018 |

(Continued)

OTHER PUBLICATIONS

International Patent Application No. PCT/US14/29843, filed Mar. 14, 2014, "Conversion of Carbon Dioxide Utilizing Chemoautotrophic Microorganisms Systems and Methods," International Preliminary Report on Patentability, Jan. 5, 2016, 99 pages.

(Continued)

*Primary Examiner* — William H. Beisner
(74) *Attorney, Agent, or Firm* — Santangelo Law Offices, P.C.

(57) ABSTRACT

Methods and systems to achieve clean fuel processing systems in which carbon dioxide emissions (1) from sources (2) may be processed in at least one processing reactor (4) containing a plurality of chemoautotrophic bacteria (5) which can convert the carbon dioxide emissions into biomass (6) which may then be used for various products (21) such as biofuels, fertilizer, feedstock, or the like. Bacteria that reduce oxidized nitrogenous species (13) may be used (Continued)

to supply reduced nitrogenous compounds to the chemoautotrophic bacteria (5).

11 Claims, 8 Drawing Sheets

(51) Int. Cl.
*C12M 1/00* (2006.01)
*B01D 53/62* (2006.01)

(52) U.S. Cl.
CPC ............ *C12N 1/20* (2013.01); *B01D 2251/95* (2013.01); *B01D 2257/504* (2013.01); *B01D 2258/0283* (2013.01); *Y02A 50/2358* (2018.01); *Y02C 10/02* (2013.01); *Y02P 20/59* (2015.11)

(56) References Cited

U.S. PATENT DOCUMENTS

| | | | |
|---|---|---|---|
| 4,760,027 | A | 7/1988 | Sublette |
| 5,173,429 | A | 12/1992 | Gaddy et al. |
| 5,593,886 | A | 1/1997 | Gaddy |
| 5,914,441 | A | 6/1999 | Hunter et al. |
| 5,981,266 | A | 11/1999 | Srivastava et al. |
| 7,118,896 | B2 | 10/2006 | Kalscheuer et al. |
| 7,285,402 | B2 | 10/2007 | Gaddy et al. |
| 7,556,094 | B1 | 7/2009 | Urynowicz |
| 7,709,624 | B2 | 5/2010 | Nakashima et al. |
| 7,832,475 | B2 | 11/2010 | Jin et al. |
| 8,127,839 | B2 | 3/2012 | Jin et al. |
| 8,268,610 | B2 | 9/2012 | Franklin et al. |
| 8,349,587 | B2 | 1/2013 | Fischer et al. |
| 8,478,444 | B2 | 7/2013 | Fuxman et al. |
| 8,633,012 | B2 | 1/2014 | Franklin et al. |
| 2001/0006809 | A1 | 7/2001 | Srivastava |
| 2003/0002236 | A1 | 1/2003 | Parent et al. |
| 2003/0066322 | A1 | 4/2003 | Perriello |
| 2005/0087449 | A1* | 4/2005 | Denvir ............ C25B 1/00 205/552 |
| 2006/0172423 | A1 | 8/2006 | Van Der Geize et al. |
| 2007/0022122 | A1 | 2/2007 | Jin et al. |
| 2008/0050800 | A1 | 2/2008 | McKeeman |
| 2008/0102515 | A1 | 5/2008 | Morales Cerda et al. |
| 2009/0193712 | A1 | 8/2009 | Verkade et al. |
| 2010/0081178 | A1 | 4/2010 | Roberts et al. |
| 2010/0120104 | A1 | 5/2010 | Reed |
| 2010/0257778 | A1 | 10/2010 | Gaertner et al. |
| 2011/0146142 | A1 | 6/2011 | Lee et al. |
| 2011/0151533 | A1 | 6/2011 | Downey et al. |
| 2011/0179699 | A1 | 7/2011 | D'addario et al. |
| 2011/0207061 | A1* | 8/2011 | Cantwell ............ C01B 13/0203 431/8 |
| 2011/0225787 | A1 | 9/2011 | Moulijn et al. |
| 2011/0244532 | A1 | 10/2011 | Hu et al. |
| 2011/0277991 | A1 | 11/2011 | Toledo et al. |
| 2011/0287497 | A1 | 11/2011 | Holtzapple et al. |
| 2012/0003705 | A1 | 1/2012 | Jin et al. |
| 2012/0064609 | A1 | 3/2012 | Clement et al. |
| 2012/0064622 | A1 | 3/2012 | Fischer et al. |
| 2012/0085705 | A1 | 4/2012 | Theodore et al. |
| 2012/0110898 | A1 | 5/2012 | Malm et al. |
| 2012/0142979 | A1 | 6/2012 | Keasling et al. |
| 2012/0244585 | A1 | 9/2012 | Kale et al. |
| 2012/0247763 | A1 | 10/2012 | Rakitsky et al. |
| 2012/0264983 | A1 | 10/2012 | Hu et al. |
| 2013/0065285 | A1 | 3/2013 | Sefton |
| 2013/0078690 | A1 | 3/2013 | Reed |
| 2013/0089899 | A1 | 4/2013 | Kurek et al. |
| 2013/0130341 | A1 | 5/2013 | Liao et al. |
| 2013/0137887 | A1 | 5/2013 | Kurosawa et al. |
| 2013/0149755 | A1 | 6/2013 | Reed et al. |
| 2013/0189739 | A1 | 7/2013 | Jin et al. |
| 2013/0189763 | A1 | 7/2013 | Dalla-Betta et al. |
| 2016/0032331 | A1 | 2/2016 | Wawrousek et al. |

FOREIGN PATENT DOCUMENTS

| | | | |
|---|---|---|---|
| EP | 0218958 | A2 | 4/1987 |
| EP | 2025755 | A1 | 2/2009 |
| EP | 2546352 | A1 | 1/2013 |
| EP | 2970859 | | 1/2016 |
| EP | 29070799 | | 10/2016 |
| WO | 9118661 | | 12/1991 |
| WO | 2007022122 | A2 | 2/2007 |
| WO | 2007109066 | A1 | 9/2007 |
| WO | 2008040365 | A1 | 4/2008 |
| WO | 2008128331 | A1 | 10/2008 |
| WO | 2008151149 | A2 | 12/2008 |
| WO | 2009002772 | | 12/2008 |
| WO | 2010120939 | A2 | 10/2010 |
| WO | 2011006019 | A2 | 1/2011 |
| WO | 2011014507 | A1 | 2/2011 |
| WO | 2011056183 | A1 | 5/2011 |
| WO | 2011071553 | A1 | 6/2011 |
| WO | 2011075163 | A1 | 6/2011 |
| WO | 2011133218 | A1 | 10/2011 |
| WO | WO-2011130407 | A1 * | 10/2011 ............... C12N 1/20 |
| WO | 2011139804 | A2 | 11/2011 |
| WO | 2011149956 | A2 | 12/2011 |
| WO | 2012154329 | A1 | 11/2012 |
| WO | 2013006912 | A1 | 1/2013 |
| WO | 2013074371 | A2 | 5/2013 |
| WO | 2013082309 | A1 | 6/2013 |
| WO | 2013148348 | A1 | 10/2013 |
| WO | 2013177471 | A2 | 11/2013 |
| WO | 2014152830 | A1 | 9/2014 |
| WO | 2014152830 | A4 | 9/2014 |
| WO | 2014200598 | A2 | 12/2014 |
| WO | 2014200598 | A3 | 12/2014 |

OTHER PUBLICATIONS

International Patent Application No. PCT/US14/27904; filed Mar. 14, 2014 entitled Methods and Systems for Biological Coal-To-Biofuels and Bioproducts, Search Report dated Aug. 29, 2014. 6 pages.
International Patent Application No. PCT/US14/27904; filed Mar. 14, 2014 entitled Methods and Systems for Biological Coal-To-Biofuels and Bioproducts, Written Opinion dated Aug. 29, 2014. 8 pages.
European Patent Application No. 14810529.9. Extended European Search Report dated Jun. 21, 2017. 14 pages.
Australian Patent Application No. 2014278749. Examination Report dated Feb. 22, 2017. 5 pages.
U.S. Appl. No. 14/776,272, filed Sep. 14, 2015. Office Action dated Apr. 3, 2017. 17 pages.
U.S. Appl. No. 14/776,272, filed Sep. 14, 2015. Restriction Requirement dated Dec. 1, 2016. 8 pages.
Australian Patent Application No. 2014236594. Examination Report dated Aug. 3, 2017. 6 pages.
European Application No. 14769071.3. Extended European Search Report dated Sep. 20, 2016. 10 pages.
U.S. Appl. No. 14/776,272, filed Sep. 14, 2015. Final Office Action dated Jan. 11, 2018. 15 pages.
Australian Patent Application No. 2014278749. Second Examination Report dated Jan. 3, 2018. 4 pages.
International Patent Application No. PCT/US14/29843; filed Mar. 14, 2014 entitled Conversion of Carbon Dioxide Utilizing Chemoautotrophic Microorganisms Systems and Methods, Search Report dated Feb. 2, 2015. 5 pages.
International Patent Application No. PCT/US14/29843; filed Mar. 14, 2014 entitled Conversion of Carbon Dioxide Utilizing Chemoautotrophic Microorganisms Systems and Methods, Written Opinion dated Feb. 2, 2014. 6 pages.
Kurosawa, et al., "High-cell-density batch fermentation of Rhodococcus opacus PD630 using a high glucose concentration of triacylglycerol production." Journal of Biotechnology 147 (2010)212-218.
Fuchtenbusch, et al., "Biosynthesis of polyhydroxyalkanoates from low-rank coal liquefaction products by Pseudomonas oleovorans and Rhodoccus tuber." Appl Microbial Biotechnol (1999) 52: 91-95.

(56) References Cited

OTHER PUBLICATIONS

Australian Patent Application No. 2014236594, filed Mar. 14, 2014. First named inventor: Wawrousek. Examination Report No. 2 for Standard Patent Application dated Apr. 18, 2018. 2 pages.
Australian Patent Application No. 2014236594, filed Mar. 14, 2014. First named inventor: Wawrousek. Notice of Acceptance for Patent Application dated May 31, 2018. 3 pages.
Australian Patent Application No. 2014278749, filed Mar. 14, 2014. Notice of Acceptance for Patent Application dated Feb. 26, 2018. 3 pages.
European Patent Application No. 14810529.9, filed Mar. 14, 2014. Communication pursuant to Article 34(3) EPC, dated Apr. 3, 2018. 4 pages.
U.S. Appl. No. 14/776,272, filed Sep. 14, 2015. First Named Inventor: Wawrousek. Office Action dated Dec. 20, 2018. 12 pages.
Viana, et al., Anaerobic digestion of crude oil glycerol: a review, Environmental Technology Reviews, vol. 1, Nov. 2012, pp. 81-92.
European Patent Application No. 14810529.9-1101, Notice of Allowance dated Jun. 14, 2019. 108 pages.
Korean Patent Application No. 10-2015-7029493, English Translation of the Office Action dated Apr. 9, 2019. 4 pages.

* cited by examiner

CONVERSION OF CARBON DIOXIDE UTILIZING CHEMOAUTOTROPHIC MICROORGANISMS SYSTEMS AND METHODS

PRIORITY CLAIM

This application is the United States National Stage of International PCT Patent Application No. PCT/US2014/029843 filed Mar. 14, 2014 which claims priority to and the benefit of U.S. Provisional Patent Application No. 61/782,762 filed Mar. 14, 2013, each application is hereby incorporated herein by reference in its entirety.

GOVERNMENT LICENSE RIGHTS

This application relates to work performed under U.S. DOE Cooperative Agreement DE-FC26-08NT43293. The U.S. government may have certain rights in this inventive technology, including "march-in" rights, as provided for by the terms of U.S. DOE Cooperative Agreement DE-FC26-08NT43293.

FIELD OF THE INVENTION

This invention relates to the technical field of clean processing systems, specifically, methods and apparatus for capturing and converting carbon dioxide emissions from fuel consumption sources or other industrial carbon dioxide emitters. Through perhaps the use of chemoautotrophic bacteria, the invention provides apparatus and methods that can be used to capture and reduce carbon dioxide emissions into the atmosphere.

BACKGROUND

Carbon sequestration is a topic receiving enormous attention in the media and among government agencies and industries involved in fuel production and use. Combustion of fossil fuels is responsible for approximately 83% of greenhouse gas emissions in the U.S. Currently, the U.S. emits $6.0 \times 10^9$ tons carbon dioxide per year and this value is expected to increase by 27% over the next 20 years. Furthermore, the reported link between increasing concentrations of greenhouse gases such as carbon dioxide ($CO_2$) in the atmosphere and global climate change has prompted several countries to adopt environmental standards that cap $CO_2$ emissions and aim to reduce current emissions. In April 2007, the U.S. Supreme Court ruled that carbon dioxide was a pollutant and that the U.S. Environmental Protection Agency (U.S. EPA) has the authority and obligation to regulate carbon dioxide emissions. The U.S. EPA has decided that carbon dioxide poses a threat to human health and the environment and that it will now be added to a list of 5 other greenhouse gases that can be regulated under the Clean Air Act. It is expected that the federal government may eventually enact a carbon cap-and-trade bill. When this occurs, utility companies, coal producers, and other industrial carbon dioxide emitters are in a position to be particularly affected by federal carbon dioxide regulation due to a large carbon dioxide footprint. An objective of the present invention may be to turn carbon dioxide into a valued resource rather than a costly expense and a liability. Embodiments of the present invention have applications in carbon dioxide capture for industrial carbon dioxide emitters, including fuel conversion sources, coal-fired power plants, natural gas-fired power plants and perhaps even distributed generation fuel cells, as well.

Most biological carbon capture and re-use technologies rely on photosynthetic microorganisms for the carbon capture. The biological techniques have been investigated since the 1970s and are now implemented at pilot-scale for carbon dioxide capture and conversion to biomass. Although algae-based technologies have shown potential for carbon dioxide capture, these technologies may be limited by the large land area that is required for adequate light penetration for optimal photosynthesis and carbon uptake rates in open ponds or by the cost of photobioreactors. These obstacles, however, may be overcome by the bacterial reactor system in the various embodiments of the present invention.

The present invention may include a Chemoautotrophic ("CAT") bacteria-based $CO_2$ consuming process for the production of biodiesel and other bio-based products. The CAT process can provide industrial carbon dioxide emitters and others with a carbon capture and re-use technology that may produce salable products perhaps thereby turning an environmental hazard and expense (such as a greenhouse gas "GHG") into a resource. If all power plant $CO_2$ emissions are converted to biodiesel such as perhaps to about 64 billion barrels of biodiesel, then the domestic transportation fuel market could be well supplied. Power plant efficiency can improve with minimal impact on the cost of electricity.

DISCLOSURE OF THE INVENTION

The present invention may provide biological carbon capture and conversion systems and methods to remove carbon dioxide from emissions. In embodiments, the present invention may integrate a carbon capture process into existing sources of carbon dioxide including but not limited to combustion power plants, mining, cement, lime and trona and refining operations, municipal waste landfills, and fuel cell plants, as a biological carbon capture and conversion system to remove carbon dioxide from emissions.

The resulting biomass produced may be reprocessed as biofuel, fertilizer, feedstock, or the like or may even be directly injected into the combustion facility (such as perhaps in co-fired applications). It is a goal of the present invention to utilize carbon dioxide as a value-added product rather than a production-limiting waste product. In this way, the carbon originally released from an industrial carbon dioxide emitter can be captured and reused at least once before release into the atmosphere.

The impacts of embodiments of the present invention may provide industrial carbon dioxide emitters and others with an economically viable carbon capture and re-use system. The described technology has the potential for a relatively rapid R&D phase, low risk to the end user in terms of long-term liability, and the ability to improve plant efficiency through biofuel production and/or co-fire applications.

It is another goal of the present invention, in embodiments, to enhance economic and energy security of the U.S. through the development of a technology that can reduce energy-related emissions of greenhouse gas and possibly improve the energy efficiency of power generation utilities and perhaps even to ensure that the U.S. can maintain a technological lead in this field. Additionally, this concept may support many goals of the Administration's Energy and Environment Agenda including investment in the next generation of energy technologies, producing more energy at home and promoting energy efficiency (perhaps through biofuel and co-fire applications for the biomass produced), closing the carbon loophole, and promoting U.S. competitiveness.

The impacts of embodiments of the present invention may provide utility companies with an environmentally responsible and economically viable carbon capture system. Furthermore, the utilization of this technology can be relatively rapid compared to other options for carbon capture, such as geologic sequestration which may still require years of testing and modeling as well as sophisticated site characterization and large capital costs with each deployment to ensure injection activities do not create a legacy of potential liability for end users and future generations of Americans. In addition to the potential for a relatively rapid R&D phase, low risk to the end user in terms of long-term liability, and the ability to improve plant efficiency through biofuel production and (or) co-fire applications, the biologic carbon capture system can almost certainly create new green jobs associated with the design, construction, maintenance and operation of these systems at power plants across the country as well as spur increased activity and innovation in the bio-processing/biofuel industries focused on utilizing the enormous quantities of biomass that can be produced.

A variety of bacteria can be developed and evaluated for $CO_2$ consumption and the biomass precursor quality from which bio-oils may be extracted and end products produced. A two bioreactor system may be advanced to facilitate reduction of oxidized nitrogenous species to reduced nitrogenous species using denitrifying bacteria, also known as nitrogen reducing bacteria ("NRB"). Reduced nitrogenous species may supply an energy source to the CAT bioreactor. The oxidized nitrogenous species, likely $NO_3$, produced in the CAT bioreactor may be recycled to generate additional reduced nitrogenous species in a first bioreactor. Acetate generated by bacteria in the NRB reactor, the nutrient conversion reactor, or both of the aforementioned reactors may be fed to bacteria in a third, acetate-conversion reactor. Biomass from the acetate-conversion reactor may be processed for bio-oils or other extractable chemicals. Non-extractable biomass fractions may be converted to nutrients to drive the bacterial system to reduce the nutrient needs. Biomass generated in the CAT, NRB, and acetate-consumption bioreactors can be processed to obtain purified lipids and other substances for processing into biodiesel, bioproducts, and other materials. Experiments may elucidate data needed to design and establish operational parameter performance and control values for a bioreactor. The bio-oils may be used as a precursor to synthesize bioproducts and petroleum replacement products.

In embodiments, acetate utilization may be integrated with the described process but using a different energy shuttle. Acetate utilization may be integrated with a process using a sulfur shuttle, which may use chemoautotrophic bacteria and sulfate reducing bacteria and may cycle sulfates and sulfides for the energy shuttle. Acetate generated by the sulfate reducing bacteria, nutrient production bacteria, or both sulfate reducing and nutrient production bacteria may be used to feed an acetate-consumption reactor for the generation of biomass and bioproducts.

Modeling and systems integration can be conducted for large-scale power plant applications and perhaps even small-scale operations such as cement and fertilizer manufacturing facilities as a "drop in" process into a conventional biodiesel plant and may even impact of different amounts of carbon capture on power plant efficiency and costs. An important aspect of the deployment project that may entail assessing market penetration for CAT biodiesel and other end products. Bio-oils can spur several domestic industries—a number of transportation fuels and other chemicals and polymers needed to sustain domestic U.S. industries and infrastructure assets, such as highways, airport runways, or the like. This may be a dramatically different approach compared to coal gasification for domestic production of such end products. The proposed concept may represent a transformational pathway to convert $CO_2$ into petroleum replacement products such as biodiesel and may even provide an efficient and economical method of capturing $CO_2$.

Naturally, further objects, goals and embodiments of the inventions are disclosed throughout other areas of the specification and claims.

MODE(S) FOR CARRYING OUT THE INVENTION

Figure 1:
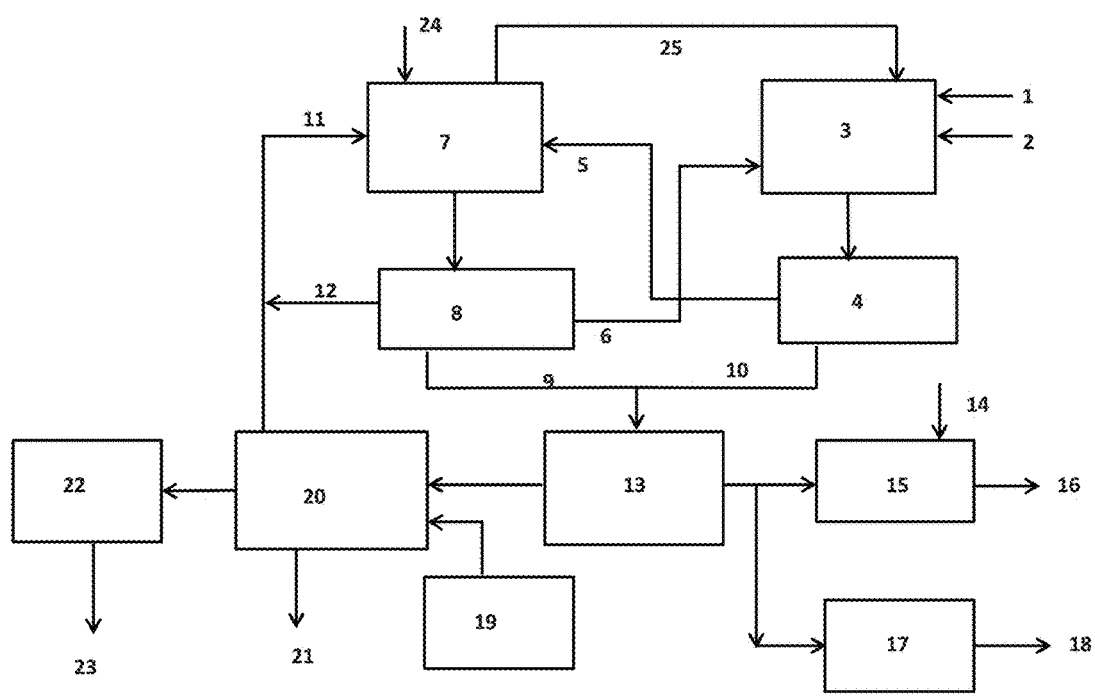
FIG. 1 shows a conceptual model of a bacterial reactor system for carbon dioxide capture and conversion into biomass in accordance with some embodiments of the present invention.

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

The present invention may provide in various embodiments, methods of reducing carbon dioxide pollutants and perhaps even processing systems for reduction of carbon dioxide pollutants. For example, a method may include but is not limited to collecting and containment of least some carbon dioxide emissions from a carbon dioxide emitting source; efficiently introducing said at least some carbon dioxide emissions from said carbon dioxide emitting source into at least one processing reactor; chemoautotrophically digesting carbon dioxide of said at least some carbon dioxide emissions with a plurality of chemoautotrophic bacteria in said at least one processing reactor; biologically producing at least some biomass from said chemoautotrophic digestion of said carbon dioxide with said chemoautotrophic bacteria; and perhaps even ecologically reducing atmospheric release of said carbon dioxide emitted from said carbon dioxide emitting source. A system may include but is not limited to a supply of at least some carbon dioxide emissions from a carbon dioxide emitting source; an emissions container configured to contain at least some of said carbon dioxide emissions from said carbon dioxide emitting source; at least one processing reactor configured to receive said at least some of said carbon dioxide emissions from said carbon dioxide emitting source; a plurality of chemoautotrophic bacteria in said at least one processing reactor configured to digest at least some of said carbon dioxide; an amount of biologically produced biomass by said chemoautotrophic bacteria located in said at least one processing reactor; and perhaps even an ecological reduction of atmospheric release of said carbon dioxide emissions from said carbon dioxide emitting source.

Initial understanding of the present invention may begin with the fact that embodiments using chemoautotrophic bacteria perhaps even in a bioreactor for carbon dioxide consumption may be combined with various technologies such as but not limited to: fuel consumption sources, power generation sources, cement and trona producing and processing plants, coal refineries, oil refineries, mining operations, lime producing plants, municipal waste facilities, non-power generation sources, coal-fired power plants, natural gas-fired power plants, fuel cells, combustion power plants, distilleries, biofuel production plants, bioproducts production plants, or the like. Fuel consumption sources may include any type of system or application in which a fuel may be consumed or perhaps even converted in the process. For example, coal is combusted in cement plants and power generation sources in the production of cement and energy and perhaps even crude oil may be converted into gasoline, diesel fuel, asphalt, or the like at refineries and the like. In embodiments, fuel conversion sources may include any system or industrial system in which carbon dioxide is generated and emitted into the atmosphere.

Generally, chemoautotrophic bacteria, such as bacteria that oxidize inorganic nitrogenous compounds, may be a candidate species to fix carbon dioxide emitted from various processes into organic molecules and biomass. Chemoautotrophic bacteria may utilize reduced nitrogen species and nitrogen containing compounds as an energy source (e.g., electron donors) and carbon dioxide as a primary carbon source. Chemoautotrophic bacteria may oxidize nitrogen containing compounds, nitrogen oxides and perhaps reduced nitrogen species, may fix carbon dioxide, and may even produce biomass as an end product. Chemoautotrophic bacteria may be a carbon dioxide emissions scrubber in which they may be utilized to scrub carbon dioxide from emissions of fuel consumption sources which may be considered a carbon dioxide capture and re-use technique.

One example of a flow process representing various embodiments of the present invention is demonstrated in FIG. 1, where at least one processing reactor (3) may be configured to receive and even process emissions such as raw flue gas from stack emissions from a fuel consumption source. A fuel consumption source may release emissions which may include a supply of carbon dioxide emissions (1) and other emissions such as nitrogen, nitrogen oxide, sulfur oxide, oxygen, combinations thereof, or the like emissions. Carbon dioxide emissions may be efficiently introduced, perhaps even passing through a heat exchanger for cooling of the emissions in some embodiments, into at least one processing reactor (3). Efficient introduction may include filtering, channeling, flowing, directing, capturing, moving, transporting, connecting (either directly or indirectly) and the like of emissions from a fuel consumption source to at least one processing reactor. A plurality of chemoautotrophic bacteria may be included in at least one processing reactor to which the plurality of chemoautotrophic bacteria may be configured to chemoautotrophically digest carbon dioxide from the emissions. Chemoautotrophic bacteria may include a plurality of bacteria of the same species or may even include a plurality of bacteria from more than one species of bacteria and may be bacteria that fix carbon and bacteria that oxidize nitrogenous compounds, such as but not limited to members of the genera *Nitrobacter, Nitrococcus, Nitrosococcus, Nitrosomonas, Nitrospria, Nitrospina, Nitrosolobus, Pedobacter* and combinations thereof. Carbon dioxide from emissions may be enzymatically transformed by the bacteria, thus some carbon may be stored in the cell biomass. The biologically produced end product biomass (4) may be predominantly amino acids, carbohydrates, and water. It is noted that the chemoautotrophic bacteria may be utilized in various carbon dioxide capture technologies with or without a processing reactor and the chemoautotrophic bacteria may be supplied from any kind of source for use in these systems. In embodiments, a processing reactor may include any type of vessel, reactor, container, system, cavern or the like.

An amount of biologically produced biomass (4) may be collected from at least one processing reactor with a biomass collector (4). In embodiments, a biomass collector (4) may include a biomass removal element for removal of biomass from at least one processing reactor such as but not limited to a concentrator, centrifuge, flotation device, settling device, filtration, or the like. The produced biomass may be readily collected and removed from the reactor to allow recycling of the medium. Biomass (4) may be processed or even converted into a product (16, 18, 23) which may include but is not limited to a fuel, salable chemical, methane, hydrogen, alcohol, fertilizer, feedstock, bioenergy, food, biofuel, biodiesel, military fuels, ethanol, plastics, animal feed, aquatic feed, food amendments, or the like. A variable amount of biomass can be produced through this process depending on the level of carbon sequestration required by the emissions source; however, even modest amounts of carbon capture and conversion may result in the production of significant amounts of biomass.

As mentioned above, the present invention may provide an energy supply perhaps even a chemoautotrophic bacteria energy supply to a plurality of chemoautotrophic bacteria which may be located in at least one processing reactor (3). The energy supply needed to drive biological carbon fixation to the chemoautotrophic bacteria in this type of reactor can be added, for example, as a supply of nitrogen containing compounds (6). Additionally, it may be possible to recycle an energy supply to the chemoautotrophic bacteria with a recycled chemoautotrophic bacteria energy supply (6) within a system and perhaps even from a second processing reactor (7) which may generate the chemoautotrophic bacteria energy supply. In some embodiments, recycled processed biomass residue may be recycled as an electron donor supply to bacteria. This may be directly or indirect use of recycled biomass residue. In some embodiments, a recycled chemoautotrophic bacteria energy supply may be recycled from within the same processing reactor. A processing reactor, or in some instances a second processing reactor (7), may include bacteria that reduce nitrogenous compounds which could reduce nitrogen species generated by the chemoautotrophic bacteria to reduced nitrogen species which can then be utilized by and even recycled to the chemoautotrophic bacteria as their energy supply. Nitrogen reducing bacteria ("NRB") may be any bacteria that can reduce oxidized nitrogenous species or participate in denitrification. Thus, in embodiments, a second processing reactor (7) may produce a supply of nitrogenous compounds and may even be a denitrifying processing reactor. A supply of nitrogenous compounds may include elemental nitrogen, ammonium, ammonia, nitrous oxide, nitric oxide, nitrite, hydroxylamine or the like which can be consumed by chemoautotrophic bacteria. Further, the NRB may also produce biomass (4) which may be collected and processed as discussed herein.

Accordingly, in embodiments, recycling of an energy supply, for example nitrogenous compounds, to the chemoautotrophic bacteria may include providing NRB in a second processing reactor (7), connecting (either directly or indirectly) at least one processing reactor (3) containing the plurality of chemoautotrophic bacteria to the second processing reactor (7) containing the nitrogenous compound reducing bacteria with perhaps a connection (5), generating oxidized nitrogen species in the least one processing reactor (3) containing the chemoautotrophic bacteria, supplying oxidized nitrogenous compounds (5) from the at least one reactor (3) containing the chemoautotrophic bacteria to the second processing reactor (7) containing the nitrogen reducing bacteria, generating nitrogenous compounds in the second processing reactor (7) containing the nitrogen reducing bacteria; and perhaps even supplying nitrogenous compounds (6) from the second processing reactor (7) containing the nitrogen reducing bacteria to the at least one processing reactor (3) with the plurality of chemoautotrophic bacteria as may be understood from FIG. 1. In this embodiment, the at least one processing reactor (3) may be configured to generate oxidized nitrogenous species (perhaps by the chemoautotrophic bacteria) and the second processing reactor (7) may be configured to generate reduced nitrogenous compounds (perhaps by the nitrogen reducing bacteria) and the two reactors may be connected (5, 6) (either directly or indirectly) so that the oxidized and reduced nitrogenous species can be supplied to the appropriate reactor. The two reactors may be physically apart from each other, may be connected or even joined by a permeable membrane or the like, or even any type of connection or attachment including but not limited to tubes, flows, pipes, or the like. In other embodiments the contents of the two reactors may be combined into one reactor and perhaps even multiple processing reactors may be used.

Alternatively, a nitrogen reducing bacteria energy supply may be provided to the nitrogen reducing bacteria which may include waste organic carbon, organic matter (19), recycled organic matter such as cell mass or other residual materials collected from the biomass or byproducts of the nitrogen reducing bacteria and chemoautotrophic bacteria (20) and recycled back to the nitrogen reducing bacteria (11), combinations thereof or the like. The nitrogen reducing bacteria energy supply may be recycled within a system or may even be supplied from an outside source. In this case, the energy input to drive the nitrogen reducing processing reactor could be in the form of waste organic carbon sources including but not limited to waste dairy products, returned milk, waste dairy byproducts, cheese whey, straw, woodchips, or the like (19). In other embodiments, a recycled process biomass residue electron donor supply may be supplied to the nitrogen reducing bacteria such that recycled process biomass residue may be used by the nitrogen reducing bacteria as an electron donor supply (20).

In embodiments and as can be understood from FIG. 1, emissions from a fuel consumption source including carbon dioxide emissions (1) and perhaps even other emissions as discussed herein may be contained as they exit the fuel consumption source perhaps even in an emissions container. An emissions container may prevent up to about 100% of the carbon dioxide emissions, in particular carbon dioxide emissions, from entering the atmosphere and may transport the emissions to at least one processing reactor (3). An emissions container may be a receptacle, filter, channel, pipe, enclosure, or the like. In embodiments, emissions may be processed prior to being introduced into the at least one processing reactor. An emission pretreatment element may pretreat the emissions perhaps even minimally to separate carbon dioxide from the other emissions. In this respect, an emission pretreatment element may be a carbon dioxide emission separator. After emissions may be treated in the emission pretreatment element, carbon dioxide may be sent (1) to at least one processing reactor (3) for carbon digestion as discussed herein.

A processing reactor (3) may contain a growth medium which may include but is not limited to bacteria, mineral salts, trace vitamins, enzymes, a commercially available enzyme for pH control, pH control, or the like. The growth medium may have adequate retention for carbon dioxide thus providing a carbon dioxide retainer but other gases such as nitrogen may flow through with perhaps practically no solubility. Bacteria such as chemoautotrophic bacteria in the processing reactor (3) may digest carbon dioxide at a digestion rate which is up to or even equal to a carbon dioxide inflow rate into the processing reactor. This may provide for optimal operation.

As biomass (4) may be removed and collected from at least one processing reactor (3) and perhaps even from a second processing reactor (7) into a biomass collector (13) it may contain both biomass and water. Water may be returned back to the processing reactor(s) or otherwise recycled into a system. These may be separated out with a separator and may even be dried in a biomass dryer to which the biomass may be further processed into various products (16, 18, 21, 23) as discussed herein. In embodiments, the biomass may be injected or even fed back into a fuel consumption source with perhaps a fuel consumption source system injector perhaps as fuel for the consumption source.

Embodiments of the present invention may also potentially extend the supply of renewable and non-renewable fuel sources such as coal, biomass or the like. Biomass produced in the processing reactor(s) may be processed into biofuel (15) such as biodiesel (16) or perhaps even ethanol or can be co-fired in the power plant, then the carbon dioxide initially liberated through combustion can be captured and re-combusted. This process can potentially recycle the carbon dioxide several times, and thereby reduce the amount of non-renewable fuel required to meet a plant's energy production goals. Further, any undigested carbon dioxide remaining in the chemoautotrophic reactor (3) or any produced carbon dioxide in the nitrogen reducing bacteria reactor (7) may be recycled. For example, an undigested carbon dioxide recycling element may recycle unprocessed carbon dioxide back into a system perhaps even back into the fuel emissions or even into an emission pretreatment element. A processing reactor may discharge other gases such as nitrogen and oxygen from the reactor and release them into the atmosphere or otherwise release these byproducts. In embodiments, waste products, impurities, contaminants or the like may be removed from the processing reactors or system as well.

Embodiments of the present invention may achieve the vision of "Clean Coal" by turning carbon dioxide into a value-added product of coal-fired power plants, as well as other fuel based consumption systems, rather than a production-limiting waste product that needs to be disposed of through costly processes (e.g., deep subsurface injection/sequestration). As can be understood from the discussion above, one concept of the system may include flue-gas injection, which may provide $CO_2$ from flue-gas, into an aqueous reactor where chemoautotrophic bacteria such as carbon-fixing bacteria may pull carbon out of solution and may incorporate it into their biological tissues and lipids (e.g., carbon fixation), perhaps effectively capturing the carbon dioxide and converting it into biomass that can be continually harvested from the processing reactor. This biomass can potentially be processed for use as fertilizer, feedstock, biofuel, or perhaps even directly injected into a combustion facility (e.g., co-fired applications) to offset the amount of coal needed to achieve the plant's Btu goals and, therefore, perhaps dilute other impurities in the flue gas such as $NO_x$ and $SO_x$ stemming from coal combustion. In this way the carbon originally released from coal combustion can be captured perhaps, significantly lowering overall net carbon dioxide generation and emissions perhaps allowing a plant to maintain power production without exceeding allowable carbon dioxide limits. Embodiments of the present invention may elucidate optimal conditions that maximize carbon assimilation rates of chemoautotrophic bacteria in a bacterial system which may include a two-part bacterial system as illustrated in FIG. 1.

In embodiments and as can be understood from FIG. 1, a system may include (1) CO2; (2) O2; (3) CAT Bioreactor; (4) CAT Biomass Harvest Gas Recovery; (5) NO3-; (6) NO2-; (7) NRB Bioreactors; (8) NRB Biomass Harvest Nutrient Recovery; (9) Bacteria; (10) Bacteria; (11) Nutrients; (12) Nutrients; (13) Lipid Extraction; (14) Methanol; (15) Biodiesel Production; (16) Biodiesel; (17) Lipid Fuels Production; (18) Lipid Fuels; (19) Alternate Residue Nutrient; (20) Nutrient Production; (21) Residue Use, Feed/Energy (High Protein), Fuel Feed; (22) Acetate; (23) CH4 via Methanogens, Chemical Feedstock, Disposal; (24) O2; (25) CO2; and any combination and permutation thereof or the like.

Figure 2:
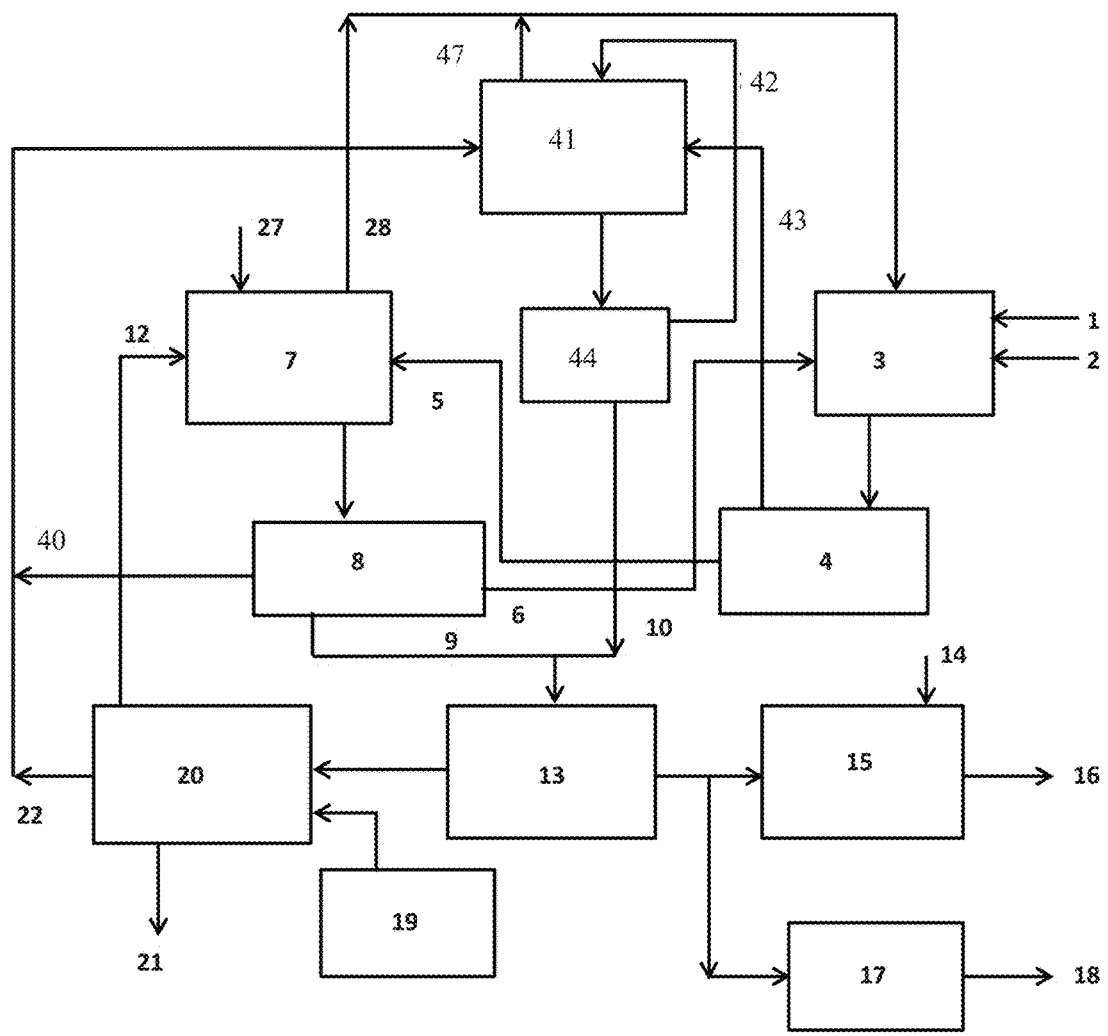
FIG. 2 shows a conceptual model of a bacterial reactor system for carbon dioxide capture and conversion into biomass with the option of an acetate conversion reactor in accordance with some embodiments of the present invention.

In embodiments and as can be understood from FIG. 2, a system may include (1) CO2; (2) O2; (3) CAT Bioreactor; (4) CAT Biomass Harvest Gas Recovery; (5) NO3-; (6) NO2-; (7) NRB Bioreactors; (8) NRB Biomass Harvest Nutrient Recovery; (9) Bacteria; (10) Bacteria; (40) Acetate; (12) Nutrients; (13) Lipid Extraction; (14) Methanol; (15) Biodiesel Production; (16) Biodiesel; (17) Lipid Fuels Production; (18) Lipid Fuels; (19) Alternate Residue Nutrient; (20) Nutrient Production; (21) Residue Use, Feed/Energy (High Protein), Fuel Feed; (22) Acetate; (41) Acetate Conversion Reactor; (42) Liquid; (43) Bacteria; (44) Biomass Harvest; (45) O2; (46) CO2; (47) CO2; and any combination and permutation thereof or the like.

In embodiments, a processing reactor may be operated in any climate, up to 24 hours a day, and may even contain a dense population of chemoautotrophic bacteria.

In embodiments, optimal conditions (e.g., pressure, temperature, and pH), nutrient concentrations (if any), concentration of nitrogenous species, inorganic carbon concentrations (e.g., $CO_2$, $HCO_3^-$, or $CO_3^{2-}$ depending on pH), inorganic ion concentrations, bacterial cell densities, and the like can be determined for maximum carbon fixation rates of various species/strains of carbon fixing bacteria. Inorganic carbon may be introduced as pure carbon dioxide for preliminary tests and then in simulated flue gas mixtures for more sophisticated tests that may also determine the lowest level of flue gas purity (i.e., least amount of pretreatment required and largest cost savings) for efficient bacterial growth and subsequent carbon capture. As discussed above, the reactor may also be equipped with a device for continuous removal of biomass followed by a device for dewatering biomass from the reactor at pre-determined cell densities to produce a bacterial paste that can be used for determining the quality of the biomass and potential applications such as biofuel production or use as a co-fired fuel for blending with coal or other fuels.

Embodiments of the present invention may include a multistep biological and chemical process for the capture and conversion of carbon dioxide and/or other sources of inorganic carbon, into organic compounds, where one or more steps in the process utilize obligate and/or facultative chemoautotrophic microorganisms, and/or cell extracts containing enzymes from chemoautotrophic microorganisms, to fix carbon dioxide or inorganic carbon into organic compounds where carbon dioxide gas alone or in a mixture or solution as dissolved carbon dioxide, carbonate ion, or bicarbonate ion including aqueous solutions such as sea water, or in a solid phase including but not limited to a carbonate mineral, is introduced into an environment suitable for maintaining chemoautotrophic organisms and/or chemoautotroph cell extracts, which fix the inorganic carbon into organic compounds, with the chemosynthetic carbon fixing reaction being driven by chemical and/or electrochemical energy provided by electron donors and electron acceptors that have been generated chemically or electrochemically or input from inorganic sources or waste sources that are made accessible through the process to the chemoautotrophic microorganisms in the chemosynthetic reaction step or steps.

Embodiments of the present invention may investigate carbon assimilation rates of chemoautotrophic bacteria such as nitrogen oxidizing and nitrifying bacteria (bacteria that fix inorganic carbon ($CO_2$) through the oxidation of chemicals rather than from sunlight). This process may use these organisms in a biological carbon capture and conversion system to remove carbon dioxide ($CO_2$) from utility and industrial facility emissions.

The proposed approach may rely on the concept that synthetic symbiosis between nitrogen reducing bacteria and nitrogen oxidizing bacteria can be sustained in a controlled manner with perhaps predictable biomass production rates in a specified operating regime. Furthermore, this may be accomplished through chemical looping of nitrogen species between nitrogen reducing heterotrophs and nitrogen oxidizing chemolithoautotrophs. In addition, the technical approach may lend itself to tailoring of the operational conditions for the harvesting of biological lipids and fatty acids perhaps for the purpose of producing biofuels and other petroleum replacement products. Also, the harvested materials may display unique attributes, in that bacteria may produce a wide range of high-valued bioproducts such as paraffin class hydrocarbons, as well as perhaps even standard biodiesel precursor lipids. The non-extractable biomass residue may be used as the nutrient source for the nitrogen reducing bacteria. The concept herein may address the deficiencies of the state of the art by producing a system that may not be reliant on an uncontrolled source of energy for the conversion of $CO_2$ into biofuels, perhaps even while providing a low-cost carbon capture technology for GHG emitting facilities.

Figure 3:
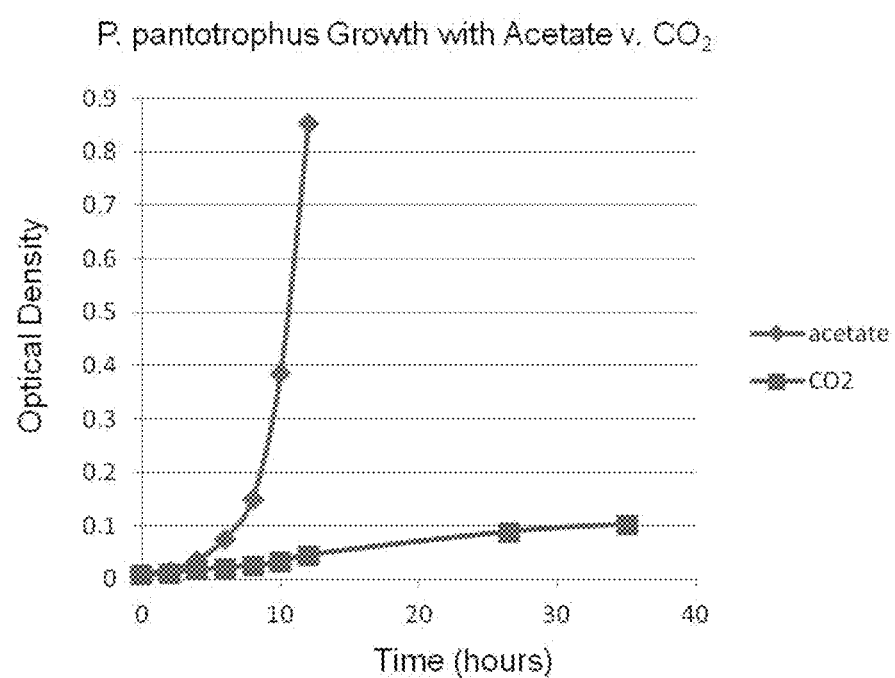
FIG. 3 is a growth curve of a selected CAT bacteria that also consumes acetate.

An acetate-consumption reactor may be introduced into the system for digestion of acetate generated in the NRB reactor, nutrient production reactor, or both reactors (FIG. 2). Bacterial growth on acetate may yield a faster growth rate, and thus a higher bacterial productivity, than growth on other carbon sources, such as carbon dioxide (FIG. 3). As waste acetate may be produced in other steps of the process, possibly in the NRB reactor, nutrient production reactor, or both reactors, use of said waste acetate to increase the amount of biomass and usable lipids produced in the system per amount of carbon dioxide consumed by the process increases the overall efficiency of the process.

A general process diagram depicting this embodiment is provided in FIG. 2, where at least one processing reactor (3) may be configured to receive and even process emissions such as raw flue gas from stack emissions from a fuel consumption source. A fuel consumption source may release emissions which may include a supply of carbon dioxide emissions (1) and other emissions such as nitrogen, nitrogen oxide, sulfur oxide, oxygen, combinations thereof, or the like emissions. Carbon dioxide emissions may be efficiently introduced, perhaps even passing through a heat exchanger for cooling of the emissions in some embodiments, into at least one processing reactor (3). Efficient introduction may include filtering, channeling, flowing, directing, capturing, moving, transporting, connecting (either directly or indirectly) and the like of emissions from a fuel consumption source to at least one processing reactor. A plurality of chemoautotrophic bacteria may be included in at least one processing reactor to which the plurality of chemoautotrophic bacteria may be configured to chemoautotrophically digest carbon dioxide from the emissions. Chemoautotrophic bacteria may include a plurality of bacteria of the same species or may even include a plurality of bacteria from more than one species of bacteria and may be bacteria that fix carbon and bacteria that oxidize nitrogenous compounds, such as but not limited to *Nitrobacter, Nitrococcus, Nitrosococcus*, and *Nitrosomonas*, and combinations thereof. These biologically based carbon dioxide capture technologies may utilize natural occurring reactions of carbon dioxide within living organisms like chemoautotrophic bacteria. Carbon dioxide from emissions may be enzymatically transformed and integrated into the bacteria, thus carbon may be stored in the cell biomass. The biologically produced endproduct biomass (4) may be dominantly amino acids, carbohydrates, and water. It is noted that the chemoautotrophic bacteria may be utilized in various carbon dioxide capture technologies with or without a processing reactor and the chemoautotrophic bacteria may be supplied from any kind of source for use in these systems. In embodiments, a processing reactor may include any type of vessel, reactor, container, system, or the like.

An amount of biologically produced biomass (4) may be collected from at least one processing reactor with a biomass collector (4). In embodiments, a biomass collector (4) may include a continuous biomass removal element for continually removing biomass from at least one processing reactor such as but not limited to a concentrator, centrifuge, filtration, setline, floatation, or the like. The produced biomass may be readily collected and removed from the reactor to allow recycling of the medium. Biomass (4) may be processed or even converted into a product (16, 18, 23) which may include but is not limited to methane, hydrogen, alcohol, fertilizer, feedstock, bioenergy, food, biofuel, biodiesel, military fuels, ethanol, plastics, animal feed and aquatic feed, food amendments, or the like; therefore, perhaps a salable end-product which can off-set operational expenses or even generate surplus profit. The process may be cost-effective in capturing carbon dioxide from emissions, let alone the side benefit from the biomass end product. The commercial value of this technology, perhaps when used in scaled up operations, could be unlimited.

A variable amount of biomass can be produced through this process depending on the level of carbon sequestration required by the emissions source; however, even modest amounts of carbon capture and conversion may result in the production of massive amounts of biomass. The ability of the Nation to become self-sufficient with sustainable energy technologies is an essential aspect for achieving energy security and, in turn, economic security and prosperity. Our consumption rate of domestic fuels may be slowed by feeding the biomass back into the plant as a fuel. This may lengthen the duration that our domestic coal can be used to achieve energy security. Utilizing the biomass to produce transportation fuels may enable lessening import of foreign oil from foreign sources.

As mentioned above, the present invention may provide an energy supply perhaps even a chemoautotrophic bacteria energy supply to a plurality of chemoautotrophic bacteria which may be located in at least one processing reactor (3). The energy supply needed to drive biological carbon fixation to the chemoautotrophic bacteria in this type of reactor can be added, for example, as a supply of nitrogen containing compounds (6). Additionally, it may be possible to recycle an energy supply to the chemoautotrophic bacteria with a recycled chemoautotrophic bacteria energy supply (6) within a system and perhaps even from a second processing reactor (7) which may generate the chemoautotrophic bacteria energy supply. In some embodiments, a recycled chemoautotrophic bacteria energy supply may be recycled from within the same processing reactor. A processing reactor, or in some instances a second processing reactor (7), may include bacteria that reduce nitrogenous compounds which could reduce nitrogen species generated by the chemoautotrophic bacteria to reduced nitrogen species which can then be utilized by and even recycled to the chemoautotrophic bacteria as their energy supply. Nitrogen reducing bacteria ("NRB") may be any bacteria that can reduce oxidized nitrogenous species. Thus, in embodiments, a second processing reactor (7) may produce a supply of nitrogenous compounds and may even be a denitrifying processing reactor. A supply of nitrogenous compounds may include elemental nitrogen, ammonia, nitrous oxide, nitric oxide, nitrite, hydroxylamine or the like which can be consumed by chemoautotrophic bacteria. Further, the NRB may also produce biomass (4) which may be collected and processed as discussed herein. The biologically produced chemoautotrophic biomass may be transferred (25) to an acetate conversion reactor (23) for enhanced growth. This carbon source used for said enhanced growth may be acetate that is generated in other reactors in the process, such as the nitrogen reducing bacteria reactor (7), the nutrient production reactor (20), or both the nitrogen reducing bacteria reactor (7) and the nutrient production reactor (20). The bacteria present in the acetate conversion reactor (23) may or may not be the same species of bacteria present in the CAT reactor (3). Biomass in produced in the acetate conversion reactor (23) may be harvested using methods similar to those previously described, and harvested biomass can be used for conversion to fuels, feed, nutrients for other bacteria in the system, and other purposes.

Accordingly, in embodiments, recycling of an energy supply, for example nitrogenous compounds, to the chemoautotrophic bacteria may include providing NRB in a second processing reactor (7), connecting (either directly or indirectly) at least one processing reactor (3) containing the plurality of chemoautotrophic bacteria to the second processing reactor (7) containing the nitrogenous compound reducing bacteria with perhaps a connection (5), generating oxidized nitrogen species in the least one processing reactor (3) containing the chemoautotrophic bacteria, supplying oxidized nitrogenous compounds (5) from the at least one reactor (3) containing the chemoautotrophic bacteria to the second processing reactor (7) containing the nitrogen reducing bacteria, generating nitrogenous compounds in the second processing reactor (7) containing the nitrogen reducing bacteria; and perhaps even supplying nitrogenous compounds (6) from the second processing reactor (7) containing the nitrogen reducing bacteria to the at least one processing reactor (3) with the plurality of chemoautotrophic bacteria as may be understood from FIG. 1. In this embodiment, the at least one processing reactor (3) may be configured to generate oxidized nitrogenous species (perhaps by the chemoautotrophic bacteria) and the second processing reactor (7) may be configured to generate reduced nitrogenous compounds (perhaps by the nitrogen reducing bacteria) and the two reactors may be connected (5, 6) (either directly or indirectly) so that the oxidized and reduced nitrogenous species can be supplied to the appropriate reactor. The two reactors may be physically apart from each other, may be connected or even joined by a permeable membrane or the like, or even any type of connection or attachment including but not limited to tubes, flows, pipes, or the like. In other embodiments the contents of the two reactors may be combined into one reactor and perhaps even multiple processing reactors may be used.

Alternatively, a nitrogen reducing bacteria energy supply may be provided to the nitrogen reducing bacteria which may include waste organic carbon, organic matter (19), recycled organic matter such as cell mass or other residual materials collected from the biomass or byproducts of the nitrogen reducing bacteria and chemoautotrophic bacteria (20) and recycled back to the nitrogen reducing bacteria (11), combinations thereof or the like. The nitrogen reducing bacteria energy supply may be recycled within a system or may even be supplied from an outside source. In this case, the energy input to drive the nitrogen reducing processing reactor could be in the form of waste organic carbon sources including but not limited to waste dairy products, returned milk, waste dairy byproducts, cheese whey, straw, woodchips, or the like (19). In other embodiments, a recycled process biomass residue electron donor supply may be supplied to the nitrogen reducing bacteria such that recycled process biomass residue may be used by the nitrogen reducing bacteria as an electron donor supply (20).

In some embodiments, acetate produced in the SRB reactor (7), the nutrient production reactor (20), or both the SRB reactor (7) and the nutrient production reactor (20) may be injected into an acetate conversion reactor (11, 22) perhaps for enhanced bacterial growth. The two reactors may be physically apart from each other, may be connected or even joined by a permeable membrane or the like as may be understood in FIG. 2, or even any type of connection or attachment including but not limited to tubes, flows, pipes, or the like. Biomass produced in the acetate conversion reactor (23) may be harvested (26) for processing of biomass and bioproducts. Lipids may be extracted for the biomass for biodiesel (16), lipid fuels (18), or both biodiesel (16) and lipid fuels (18). Biomass residue may be processed (20) to provide nutrients to the SRB (12). In some embodiments, biomass residue may also be used for the production of animal and aquatic feed, fuels, and other purposes. In some embodiments, acetate, biomass residue, or acetate and biomass residue may also be fed to bacteria for the production of methane (21).

In embodiments and as can be understood from FIG. 1, emissions from a fuel consumption source including carbon dioxide emissions (1) and perhaps even other emissions as discussed herein may be contained as they exit the fuel consumption source perhaps even in an emissions container. An emissions container may prevent up to about 100% of the carbon dioxide emissions, in particular carbon dioxide emissions, from entering the atmosphere and may transport the emissions to at least one processing reactor (3). An emissions container may be a receptacle, filter, channel, pipe, enclosure, or the like. In embodiments, emissions may be processed prior to being introduced into the at least one processing reactor. An emission pretreatment element may pretreat the emissions perhaps even minimally to separate carbon dioxide from the other emissions. In this respect, an emission pretreatment element may be a carbon dioxide emission separator. After emissions may be treated in the emission pretreatment element, carbon dioxide may be sent (1) to at least one processing reactor (3) for carbon digestion as discussed herein.

A processing reactor (3) may contain a growth medium which may include but is not limited to bacteria, mineral salts, trace vitamins, enzymes, a commercially available enzyme for pH control, pH control, or the like. The growth medium may have adequate retention for carbon dioxide thus providing a carbon dioxide retainer but other gases such as nitrogen may flow through with perhaps practically no solubility. Bacteria such as chemoautotrophic bacteria in the processing reactor (3) may digest carbon dioxide at a digestion rate which is up to or even equal to a carbon dioxide inflow rate into the processing reactor. This may provide for optimal operation.

As biomass (4) may be removed and collected from at least one processing reactor (3) and perhaps even from a second processing reactor (7) into a biomass collector (13) it may contain both biomass and water. Water may be returned back to the processing reactor(s) or otherwise recycled into a system. These may be separated out with a separator and may even be dried in a biomass dryer to which the biomass may be further processed into various products (16, 18, 21, 23) as discussed herein. In embodiments, the biomass may be injected or even fed back into a fuel consumption source with perhaps a fuel consumption source system injector perhaps as fuel for the consumption source.

Embodiments of the present invention may also potentially extend the supply of renewable and non-renewable fuel sources such as coal, biomass or the like. Biomass produced in the processing reactor(s) may be processed into biofuel (15) such as biodiesel (16) or perhaps even ethanol or can be co-fired in the power plant, then the carbon dioxide initially liberated through combustion can be captured and re-combusted. This process can potentially recycle the carbon dioxide several times, and thereby reduce the amount of non-renewable fuel required to meet a plant's energy production goals. Further, any undigested carbon dioxide remaining in the chemoautotrophic processing reactor (3) or any produced carbon dioxide in the nitrogen reducing bacteria reactor (7) may be recycled. For example, an undigested carbon dioxide recycling element may recycle unprocessed carbon dioxide back into a system perhaps even back into the fuel emissions or even into an emission pretreatment element. A processing reactor may discharge other gases such as nitrogen and oxygen from the reactor and release them into the atmosphere or otherwise release these byproducts. In embodiments, waste products, impurities, contaminants or the like may be removed from the processing reactors or system as well.

In an alternate embodiment, a sulfur shuttle may be used in the described process. If a sulfur energy shuttle is used, chemoautotrophic sulfur oxidizing bacteria may be used to consume carbon dioxide while oxiding a reduced sulfur species, likely a sulfide, to form a sulfate. The sulfate can be transported and injected into a reactor containing sulfate reducing bacteria (SRB), in which the sulfate can be reduced to form $H_2S$. Produced $H_2S$ can by cycled back to the CAT reactor for oxidation by the CAT bacteria.

Generally, chemoautotrophic bacteria, such as sulfur-oxidizing bacteria, may be a candidate species to fix carbon dioxide emitted from various processes. Chemoautotrophic bacteria may utilize elemental sulfur, various sulfide minerals, sulfur containing compounds, or other products as an energy source (e.g., electron donors) and carbon dioxide as their primary carbon source. Chemoautotrophic bacteria may efficiently oxidize sulfur containing compounds, sulfur and perhaps even sulfides, may fix carbon dioxide, and may even produce biomass or perhaps even high cell biomass as an end product. Chemoautotrophic bacteria may be a carbon dioxide emissions scrubber in which they may be utilized to scrub carbon dioxide from emissions of fuel consumption sources which may be considered a carbon dioxide capture technique for the purpose of meeting emission values imposed by cap and trade legislation or the like.

Figure 4:
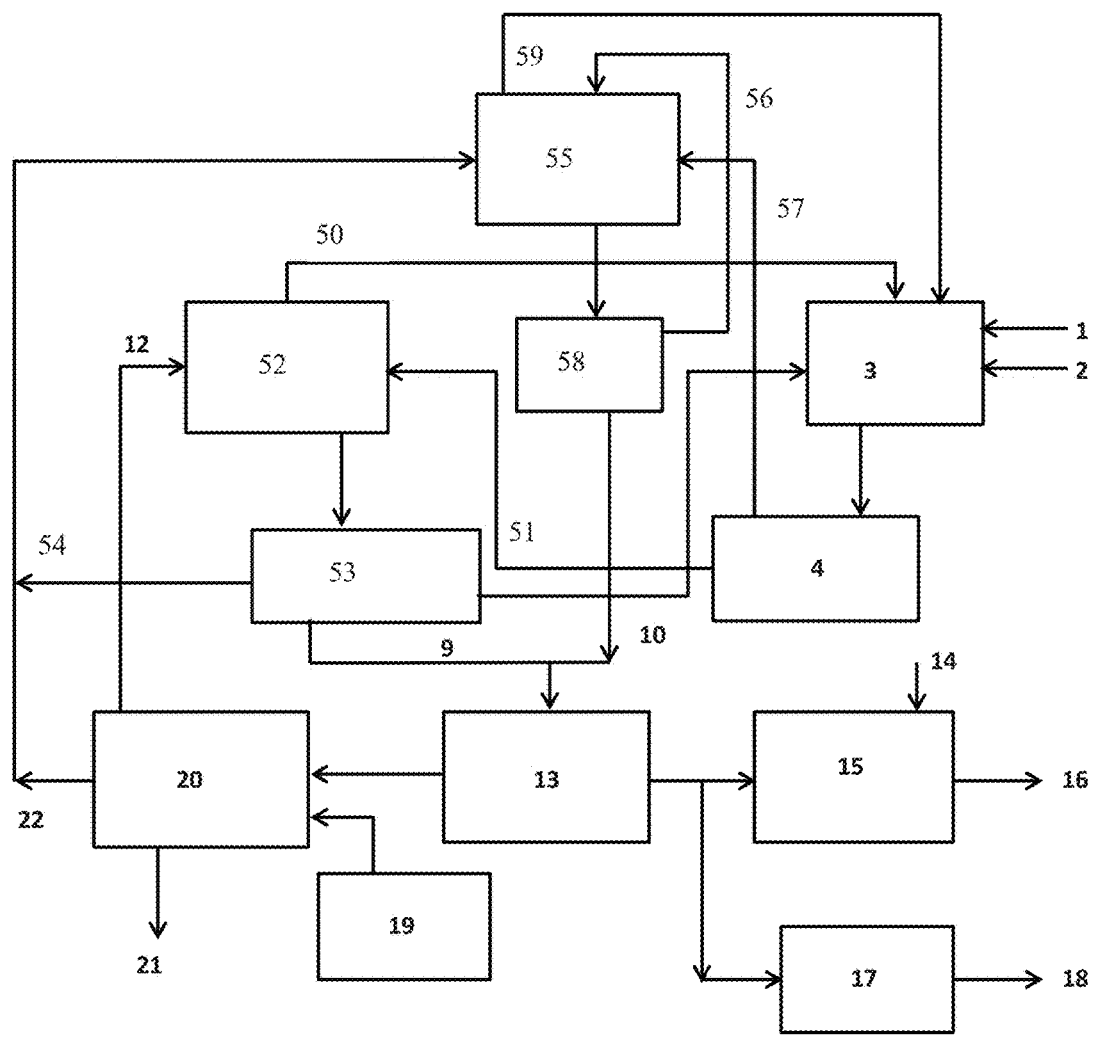
FIG. 4 is a conceptual model of a bacterial reactor system for carbon dioxide capture and conversion into biomass using a sulfur shuttle with the option of an acetate-consumption reactor in accordance with some embodiments of the present invention.

One example of a flow process representing various embodiments of the present invention is demonstrated in FIG. 4, where at least one processing reactor (3) may be configured to receive and even process emissions (1) such as raw flue gas from stack emissions from a fuel consumption source. A fuel consumption source may release emissions which may include a supply of carbon dioxide emissions (1) and other emissions (2) such as nitrogen, nitrogen oxide, sulfur oxide, oxygen, combinations thereof, or the like emissions. Carbon dioxide emissions may be efficiently introduced, perhaps even passing through a heat exchanger for cooling of the emissions in some embodiments, into at least one processing reactor (3). Efficient introduction may include filtering, channeling, flowing, directing, capturing, moving, transporting, connecting (either directly or indirectly) and the like of emissions from a fuel consumption source to at least one processing reactor. A plurality of chemoautotrophic bacteria may be included in at least one processing reactor (3) to which the plurality of chemoautotrophic bacteria may be configured to chemoautotrophically digest carbon dioxide from the emissions. Chemoautotrophic bacteria may include a plurality of bacteria of the same species or may even include a plurality of bacteria from more than one species of bacteria and may be carbon fixing bacteria and sulfur oxidizing bacteria, such as but not limited to members of the genera *Paracoccus* and *Thiobacillus*, and combinations thereof. These biologically based carbon dioxide capture technologies may utilize natural occurring reactions of carbon dioxide within living organisms like chemoautotrophic bacteria. Carbon dioxide from emissions may be enzymatically transformed and integrated into the bacteria, thus carbon may be stored in the cell biomass. The biologically produced end product biomass (25) may be transferred to an acetate conversion reactor for enhanced growth. This carbon source used for said enhanced growth may be acetate that is generated in other reactors in the process, such as the sulfate reducing bacteria reactor (7), the nutrient production reactor (20), or both the sulfate reducing bacteria reactor (7) and the nutrient production reactor (20). The bacteria present in the acetate conversion reactor (23) may or may not be the same species of bacteria present in the CAT reactor (3). Biologically produced biomass may be dominantly amino acids, carbohydrates, and water. It is noted that the chemoautotrophic bacteria may be utilized in various carbon dioxide capture technologies with or without a processing reactor and the chemoautotrophic bacteria may be supplied from any kind of source for use in these systems. In embodiments, a processing reactor may include any type of vessel, reactor, container, system, or the like.

In embodiments and as can be understood from FIG. 4, a system may include CO2 (1); O2 (2); a CAT Bioreactor (3); a CAT Biomass Harvest Gas Recovery (4); S2- (50); SO42-; (51); SRB Bioreactors (52); SRB Biomass Harvest Nutrient Recovery (53); Bacteria (9); Bacteria (10); Acetate (54); Nutrients (12); Lipid Extraction (13); Methanol (14); Biodiesel Production (15); Biodiesel (16); Lipid Fuels Production (17); Lipid Fuels (18); Alternate Residue Nutrient (19); Nutrient Production (20); Residue Use (20), Feed/Energy (High Protein), Fuel Feed (21); Acetate (22); Acetate Conversion Reactor (55); Liquid (56); Bacteria (57); Biomass Harvest (56); CO2 (59); and any combination and permutation thereof or the like.

In an alternative embodiment, biomass may be harvested from the CAT reactor (3) for processing of biomass and bioproducts. In an alternative embodiments, enhanced bacterial growth on acetate in the acetate conversion reactor may not be seeded with CAT bacteria. Perhaps the acetate conversion bacteria may be a separate species or strain from the CAT bacteria, necessitating biomass harvesting for biomass and bioproduct processing from both the CAT reactor and acetate conversion reactor.

An amount of biologically produced biomass (8, 26) may be collected from at least one processing reactor with a biomass collector. In embodiments, a biomass collector may include a continuous biomass removal element for continually removing biomass from at least one processing reactor such as but not limited to a concentrator, centrifuge, diskstack centrifuge, or the like. The produced biomass may be readily collected and removed from the reactor to allow recycling of the medium. Biomass (9, 10) may be processed or even converted into a product (16, 18, 21) which may include but is not limited to methane, hydrogen, alcohol, fertilizer, feedstock, bioenergy, food, biofuel, biodiesel, military fuels, ethanol, plastics, animal feed, food amendments, or the like; therefore, perhaps a sellable end-product which can off-set operational expenses or even generate surplus profit. The process may be cost-effective in capturing carbon dioxide from emissions, let alone the side benefit from the biomass end product. The commercial value of this technology, perhaps when used in scaled up operations, could be unlimited. A variable amount of biomass can be produced through this process depending on the level of carbon sequestration required by the emissions source; however, even modest amounts of carbon capture and conversion may result in the production of significant amounts of biomass.

As mentioned above, the present invention may provide an energy supply (2) perhaps even a chemoautotrophic bacteria energy supply to a plurality of chemoautotrophic bacteria which may be located in at least one processing reactor (3). The energy supply (2) needed to drive biological carbon fixation to the chemoautotrophic bacteria in this type of reactor can be added, for example, as a supply of sulfur containing compounds such as metal sulfides, hydrogen sulfide ($H_2S$) or perhaps even elemental sulfur, of which there may be large stockpiles worldwide as this is a waste product of the oil refining process. Additionally, it may be possible to recycle an energy supply to the chemoautotrophic bacteria with a recycled chemoautotrophic bacteria energy supply (5) within a system and perhaps even from a second processing reactor (7) which may generate the chemoautotrophic bacteria energy supply. In some embodiments, a recycled chemoautotrophic bacteria energy supply may be recycled from within the same processing reactor. A processing reactor, or in some instances a second processing reactor (7), may include sulfate reducing bacteria which could reduce sulfate generated by the chemoautotrophic bacteria to sulfides to which the sulfides can then be utilized by and even recycled to the chemoautotrophic bacteria as their energy supply. Sulfate reducing bacteria ("SRB") may be a sulfur or even a sulfate reducing bacteria and may even include any bacteria that can reduce oxidized sulfur species. Thus, in embodiments, a second processing reactor (7) may produce a supply of sulfur containing compounds (5) and may even be a sulfate-reducing processing reactor. A supply of sulfur containing compounds (5) may include elemental sulfur, sulfides, metal sulfides, hydrogen sulfide, or the like which can be consumed by chemoautotrophic bacteria. Further, the sulfate-reducing bacteria may also produce biomass (8) which may be collected and processed as discussed herein.

Accordingly, in embodiments, recycling of an energy supply, for example sulfur containing compounds, to the chemoautotrophic bacteria may include providing sulfate reducing bacteria in a second processing reactor (7), connecting (either directly or indirectly) at least one processing reactor (3) containing the plurality of chemoautotrophic bacteria to the second processing reactor (7) containing the sulfate reducing bacteria with perhaps a connection (6), generating sulfate or other oxidized sulfur species in the least one processing reactor (3) containing the chemoautotrophic bacteria, supplying sulfate or oxidized sulfur (6) from the at least one reactor (3) containing the chemoautotrophic bacteria to the second processing reactor (7) containing the sulfate reducing bacteria, generating sulfur containing compounds (5) in the second processing reactor (7) containing the sulfate reducing bacteria; and perhaps even supplying sulfur containing compounds (5) from the second processing reactor (7) containing the sulfate reducing bacteria to the at least one processing reactor (3) with the plurality of chemoautotrophic bacteria as may be understood from FIG. 4. In this embodiment, the at least one processing reactor (3) may be configured to generate sulfate or oxidized sulfur (6) (perhaps by the chemoautotrophic bacteria) and the second processing reactor (7) may be configured to generate sulfur containing compounds or reduced sulfur (5) (perhaps by the sulfate reducing bacteria) and the two reactors may be connected (5, 6) (either directly or indirectly) so that the sulfate and sulfur, or even the oxidized and reduced sulfur, can be supplied each other. The two reactors may be physically apart from each other, may be connected or even joined by a permeable membrane or the like as may be understood in FIG. 4, or even any type of connection or attachment including but not limited to tubes, flows, pipes, or the like. In other embodiments the contents of the two reactors may be combined into one reactor and perhaps even multiple processing reactors may be used.

Alternatively, a sulfate reducing bacteria energy supply (19) may be provided to the sulfate reducing bacteria which may include waste organic carbon, organic matter, recycled organic matter such as cell mass or other residual materials collected from the biomass or byproducts of the sulfate reducing bacteria and recycled back to the sulfate reducing bacteria, combinations thereof or the like. The sulfate reducing bacteria energy supply (19, 20) may be recycled within a system or may even be supplied from an outside source. In this case, the energy input to drive the sulfate reducing processing reactor could be in the form of waste organic carbon sources including but not limited to waste dairy products, returned milk, waste dairy byproducts, cheese whey, straw, woodchips, or the like. In other embodiments, a recycled process biomass residue electron donor supply (20) may be supplied to the sulfate reducing bacteria such that recycled process biomass residue may be used by the sulfate reducing bacteria as an electron donor supply.

Acetate produced in the SRB reactor (7), the nutrient production reactor (20), or both the SRB reactor (7) and the nutrient production reactor (20) may be injected into an acetate conversion reactor (11, 22) perhaps for enhanced bacterial growth. The two reactors may be physically apart from each other, may be connected or even joined by a permeable membrane or the like as may be understood in FIG. 4, or even any type of connection or attachment including but not limited to tubes, flows, pipes, or the like. Biomass produced in the acetate conversion reactor (23) may be harvested (26) for processing of biomass and bioproducts. Lipids may be extracted for the biomass for biodiesel (16), lipid fuels (18), or both biodiesel (16) and lipid fuels (18). Biomass residue may be processed (20) to provide nutrients to the SRB (12). In some embodiments, biomass residue may also be used for the production of animal feed and aquatic feed, fuels, and other purposes. In some embodiments, acetate, biomass residue, or acetate and biomass residue may also be fed to bacteria for the production of methane (21).

Figure 6:
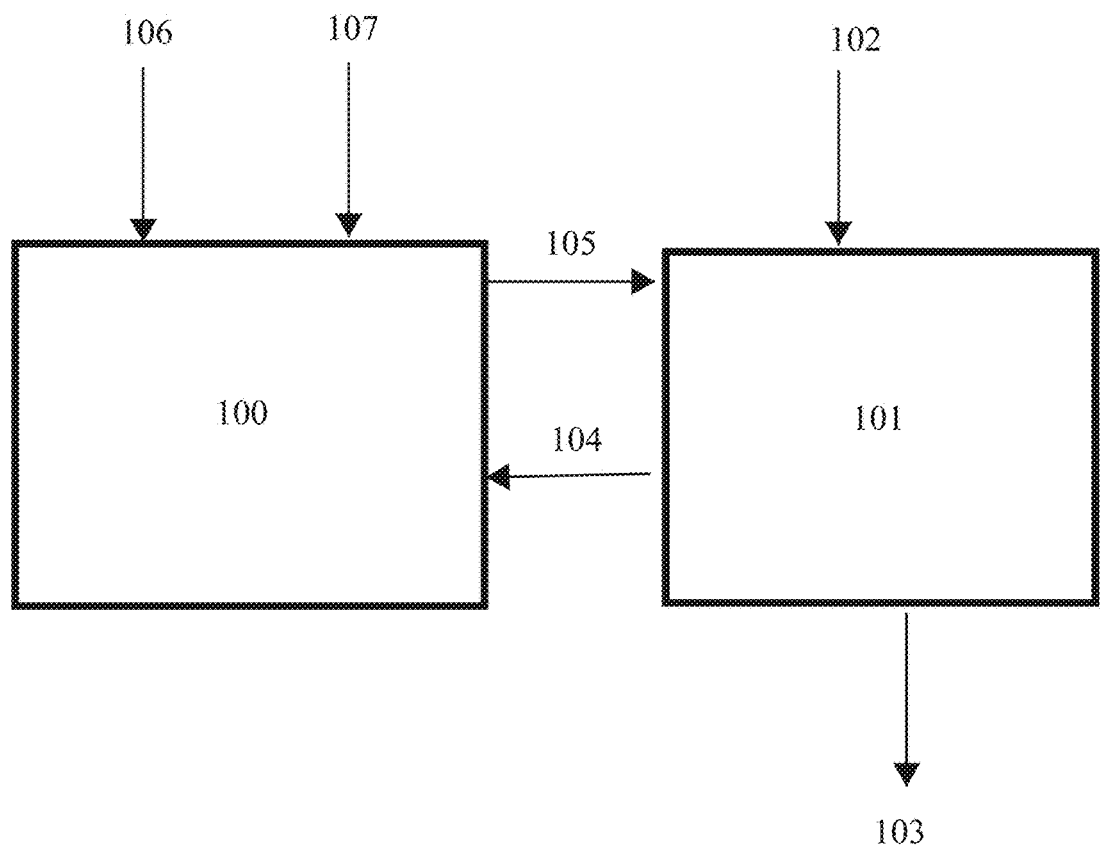
FIG. 6 shows a conceptual model of a bacterial reactor system for carbon dioxide capture and conversion into biomass using nitrifying and ammonifying microorganisms in accordance with some embodiments of the present invention.

In various embodiments, and as may be understood from FIG. 6, at least one processing reactor (100) may provide nitrification perhaps aerobic nitrification. CO2 (106) and even O2 (107) may be introduced into the reactor (100). CO2 may be converted into biomass in this reactor. CAT bacteria may generate NO3 (105) which may be fed perhaps by a feed supply to at least one additional processing reactor (101). The reactor (101) may be an ammonifying reactor which may contain ammonifying bacteria and reactor (101) may even generate biomass that can be harvested, used, or reused. NO3 from reactor (100) may be converted to NH3. Elements may be added to the reactor (101) such as but not limited to fumerate, nutrients, or the like. NH3 from reactor (101) may be fed perhaps by a feed supply to reactor (100). Reactor (100) may utilize the NH3 to generate NO2 which could then generate NO3. It is noted that any supply, feed, or the like may be understood as a feed supply of an element to a bacteria or reactor or the like.

Figure 7:
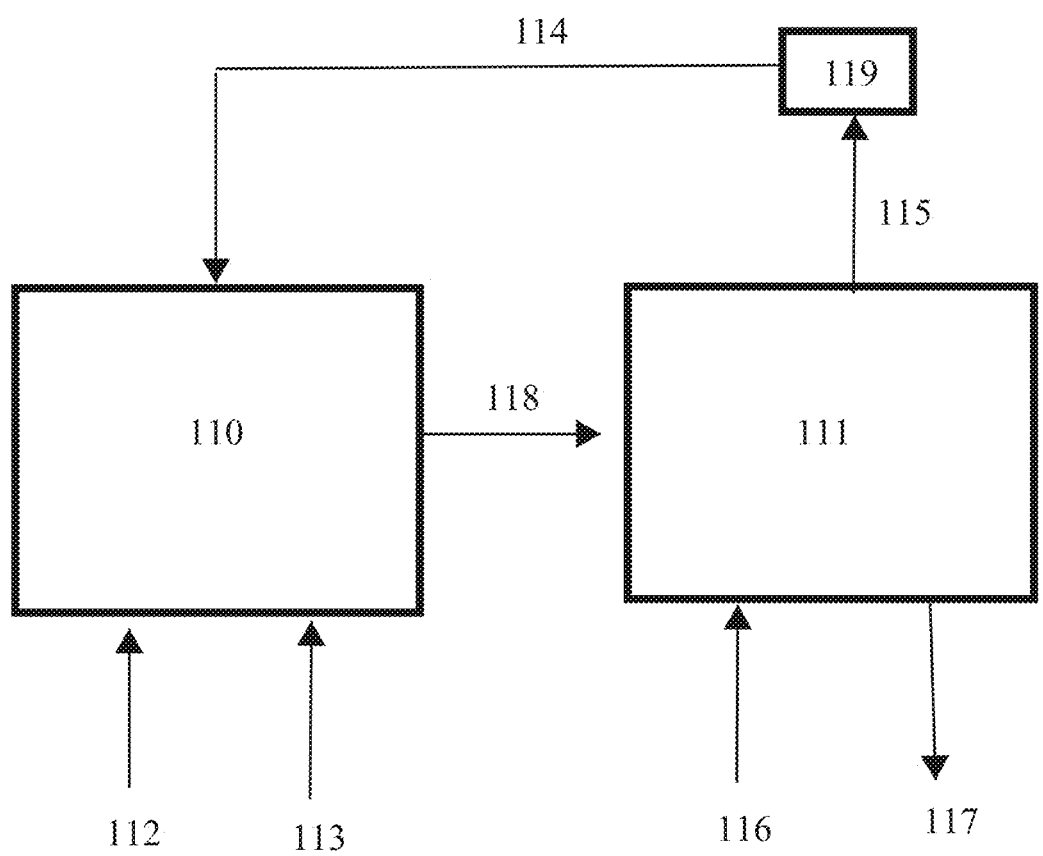
FIG. 7 shows a conceptual model of a bacterial reactor system for carbon dioxide capture and conversion into biomass using nitrifying and denitrifying bacteria in accordance with some embodiments of the present invention.

In various embodiments, and as may be understood from FIG. 7, at least one processing reactor (110) may provide nitrification perhaps aerobic nitrification. CO2 (112) and even O2 (113) may be introduced into the reactor (100). CO2 may be converted into biomass in this reactor. CAT bacteria may generate NO3 (118) which may be fed perhaps by a feed supply to at least one additional processing reactor (111). The reactor (111) may be a denitrification reactor perhaps a denitrification anaerobic reactor which may contain denitrification bacteria. Reactor (111) may generate biomass that may be harvested, used, or reused. NO3 from reactor (110) may be converted to N2. N2 (115) may be processed (119), perhaps via Haber process, to generate NH3 (114) which may be fed into reactor (110). Elements may be added to the reactor (111) such as but not limited to ethanol, nutrients, or the like. Reactor (110) may utilize the NH3 to generate NO2 which could then generate NO3. CO2 and other elements (117) may be generated and may be removed from reactor (111).

Figure 8:
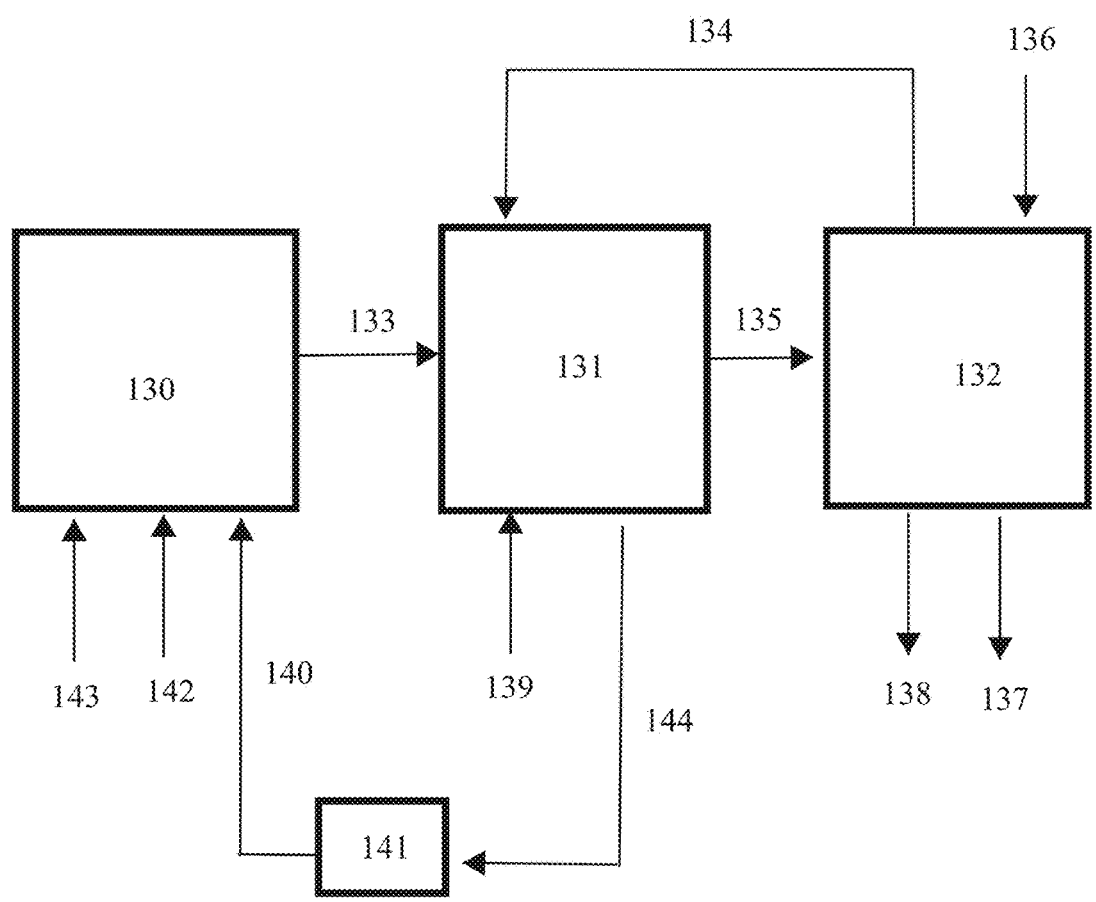
FIG. 8 shows a conceptual model of a bacterial reactor system for carbon dioxide capture and conversion into biomass using nitrifying and denitrifying bacteria without recycle of the inorganic shuttling material in accordance with some embodiments of the present invention.

In various embodiments, and as may be understood from FIG. 8, at least two inorganic processes may be utilized. At least one processing reactor (130) may include CAT bacteria and may even provide nitrification, perhaps aerobic nitrification. Reactor (130) may contain sulfur oxidizing nitrate reducing bacteria. CO2 (143) and even O2 (142) may be introduced into the reactor (130). CO2 may be converted into biomass in this reactor. CAT bacteria may generate NO3 (133) which may be fed perhaps by a feed supply to at least one additional processing reactor (131). A reactor (131) may be a denitrification reactor perhaps a denitrification anaerobic reactor which may contain denitrification bacteria such as but not limited to *Thiobacillus denitrificans*. Reactor (131) may generate biomass that may be harvested, used, or reused. NO3 from reactor (130) may be converted to N2. CO2 (139) may be introduced into reactor (131). N2 (144) may be processed (141), perhaps via Haber process, to generate NH3 (140) which may be fed into reactor (130). In some embodiments, NH4 or NH3 may be supplied to reactor (130) from a different source and may not have been recycled. Reactor (131) may generate SO4 (135) which may be fed perhaps via a feed supply to at least one additional reactor (132). Reactor (132) may be a SRB reactor and perhaps even an anaerobic reactor, which may contain sulfide reducing bacteria. SO4 may be utilized to generate sulfide. Lactate (136) or other elements such as but not limited to nutrients or the like may be introduced into reactor (132). Lactate may be converted into CO2 and biomass. Biomass may be generated in reactor (132) which may be harvested, used, or reused. Reactor (132) may generate acetate (138) and even CO2 (137) which may be removed from the reactor for other uses. Sulfide (134) may be fed perhaps by a feed supply into reactor (131). Of course, in each of the figures, elements may be introduced into reactors, may be removed from reactors, may be recycled, or may even be collected and not recycled in various embodiments.

Embodiments of the invention may address specific societal goals in that it (1) may enhance economic and energy security of the U.S. through the development of a technology that could produce energy-dense, infrastructure compatible liquid fuels from $CO_2$ perhaps as the only carbon source thereby reducing petroleum imports (2) may effectively capture stationary sources of energy-related emissions of greenhouse gases (GHG), (3) may improve the energy efficiency of GHG emitting facilities, such as power generation utilities and industrial and manufacturing facilities, and perhaps even (4) may ensure that the U.S. could maintain a technological lead in this field. Additionally, the concept may support many of the goals of the US administration including investment in the next generation of energy technologies, producing more energy at home and promoting energy efficiency (by producing biofuels and bioproducts that store carbon), and perhaps even promoting U.S. competitiveness. As such, the technology can bring about a transformation of the industry, providing a leap in advancement to overcome a number of obstacles that are currently limiting the deployment of biofuels and carbon capture for retrofitting utility and industrial GHG facilities for GHG emissions control.

Alternate embodiments of the present invention may include $CO_2$ removed from a flue gas and injection into an aqueous reactor where carbon-fixing bacteria may use carbon and incorporate it into their biological tissues and lipids.

The process may capture $CO_2$ using chemoautotrophic bacteria in an anaerobic bioreactor, which may be fueled by reduced nitrogenous species supplied by perhaps a separate bioreactor occupied by perhaps nitrogen reducing bacteria ("SRB"). The nitrate or oxidized nitrogenous species generated as a product of oxidation of reduced nitrogenous species in the CAT bioreactor may be used as a source of electron acceptors for making reduced nitrogenous species (electron donors) in the anaerobic system. The biomass may be harvested from the bioreactor and processed into biofuel and/or petroleum replacement products. The residual biomass from the oil extraction may be used as the nutrient source for the process. Oil yields may be estimated to be sufficient to provide residual biomass to meet the nutrient needs of the process.

Biofuels may be currently one of the few commercial alternatives to continued dependency on oil. The Energy Independence and Security Act of 2007 (EISA) established a goal of 36 billion gallons of biofuels by 2022 to power our cars, trucks, jets, ships, mining equipment, locomotives and tractors. In 2010, only 12 billion gallons of biofuels are produced annually. The EIA's reference case for the 2010 Annual Outlook projects that most of the growth in liquid fuel supply will be met by biofuels—yet EIA also projects that the industry will not meet the 2022 goal. The existing biofuels industry represents three generations of fuels that in their own right were transformational and market disruptive.

The first-generation agricultural-based ethanol biofuels industry has grown from 1% of the U.S. fuel supply to 7% in 2008. However, the Renewable Fuel Standard in the EISA has effectively placed a 15 billion gallon cap on ethanol production from corn as part of the new 36 billion gallon target for 2022. The remainder of the target has to be met with second and third generation advanced biofuels, including cellulosic ethanol, biobutanol, biobased diesel, and other biofuels that are a direct replacement for petroleum-based fuels.

While corn ethanol has played a key role in establishing the U.S. biofuel industry, it remains controversial, due in part to the fact that using corn for biofuels displaces crops that would otherwise have been used for humans, requires high water use, and requires high amounts of land. Recent estimates are that corn based ethanol has replaced 32% of the corn crop in the U.S. for ethanol production.

While cellulosic ethanol may hold great promise, the lack of commercial-scale facilities in operation has created a degree of uncertainty regarding the true operating expenses required for producing cellulosic ethanol. While cellulosic ethanol is transformational over corn based ethanol, unmodified engines may be unable to process volumetric blends above 10% ethanol without significant damage. Although Flex Fuel Vehicles (FFVs) enable the driver to choose between using gasoline or ethanol blends up to 85%

(E85), market acceptance in the U.S. is very low, since only 1% of U.S. gas stations offer E85 ethanol pumps. The third-generation of biofuels, based on algae may allow for the production of 'drop-in fuels' while also making use of the pre-existing petroleum infrastructure. As such, algae may secrete lipids with chemical compositions similar to petroleum-based hydrocarbons. Algae-based fuels may have growth pattern and harvesting processes qualitatively different from any other alcohol- or oil-producing biomass. Algae, due to their high oil yield (up to about 50× the amount of biofuel compared to other leading feedstocks), uptake and cycling of $CO_2$, and perhaps even capacity to be grown on marginal land in brackish and/or saline water may have spurred its development. Algae may have yields of about 2,000 gallons per acre per year in open ponds and yields may be increased up to about 10,000 gallons per acre per year, depending upon the genetically modified organisms ("GMO") strains that are used and perhaps even the utilization of photobioreactors (PBRs). However, those strains that produce high yields may also tend to have slower growth rates, thereby creating even higher land burdens for production.

The proposed chemoautotrophic-based technologies may be the fourth generation biofuel with perhaps equivalent transformational and market disruption attributes that the third generation algae-based biofuels industry had over the first and second generation ethanol biofuels. Like third-generation biofuels, the bacteria-based technologies may allow for 'drop in' fuels that replace and are compatible with petroleum-based fuels, not solely as an additive. Although CAT based systems may not produce a very high lipid content, they may have unique compositions that may allow for other very high valued other products such as essential equivalent lipid yields with bacteria as with algae.

Due to the fact that CAT based systems do not need sunlight for growth, the land area required for the CAT bacteria growth may be about $1/50^{th}$ the size needed for open algae-based production and may be about $1/10^{th}$ the size for algae in photobioreactors that need expensive energy-consuming artificial lighting. Fourth-generation bio-fuels, due to their smaller footprint, may be more amenable to be co-located with small local and large $CO_2$ sources, such as power plants.

Biofuels production may not be the only benefit of bacteria-based systems. Emerging bacteria-based biofuels production processes may also be carbon capture technologies. According to the EIA, the United States energy industry emitted over 5.9 billion metric tonnes of $CO_2$ in 2006 and is projected to emit over 6.4 billion metric tonnes/yr by 2030, an 8% increase in emissions. Those fuels with the largest emissions are coal and oil, with 2.5 and 2.6 billion metric tonnes/year, respectively. As a result of climate change debate, the U.S. is considering mandatory reductions in $CO_2$ in incremental stages, as such 5% additional reduction of $CO_2$ per every 5 years in order to qualify for credits.

The value to the carbon-dioxide emitting source of an alternate carbon capture and storage technology such as bacteria-based capture which may not significantly increase parasitic power can be calculated from these COE increases. For example, the total value to the utility of about 65% carbon capture on the about 550 MWe plant may result in about 10.4 cents/kWh, based on interpolated DOE's data between zero and about 90% percent capture. Assuming values of about 8000 hrs of annual plant operation and about 550 MWe net electric output, the total additional cost that would be incurred to meet about 65% CCS is estimated to be about $176 million annually. Clearly, the implementation of the proposed CAT bacteria biofuels process could significantly reduce the economic burden of carbon capture on the utility and the ratepayers, but also on the economics of the biofuels produced, enhancing energy and environmental security.

There may be an ongoing development in the area of bacteria-based biofuels. Although most bacteria generate complex lipid for specified chemical production, it has been reported that some bacteria can accumulate oils under some special conditions. Development of bacteria based biofuels and other energy related technologies have started to gain momentum in industrial applications. Some applications may include supplementing algae systems during non peak sunlight conditions to perhaps increase production. Other trends in the field include Amery's focus on utilizing bacteria as a micro-refinery by feeding the bacteria sugar cane and then 'milking the microbe' to secrete synthetic diesel. The microbe (e.g., algae, bacteria and the like) may be a mini-processor of biomass feedstock directly into fuels. Other companies may appear to have engineered both yeast and *E. coli* bacteria to make use of previously undiscovered metabolic pathways to convert sugars into hydrocarbon products than can be put straight into your gas tank, or perhaps even sent off to a refinery for processing. This may be nearly carbon neutral and may be about 65 percent less energy intensive than ethanol fermentation. Chen has demonstrated that methane production may be possible from reverse microbial fuel cell. In this application, the nutrient source may typically be acetate and a voltage may be applied across the cell to increase and/or perhaps stimulate the oxidation of the nutrient source. Embodiments of the present invention may be totally different from these technologies due to its use of a nitrogen-based shuttle. Dual bacteria species may be used, the conversion of residue to supply the nutrients needed, (as opposed to use of external waste streams as the nutrient source), the potential use of waste acetate generated in the system as a nutrient, and the production of biodiesel and other bioproducts are examples of the process differences.

Embodiments of the present invention may include a CAT bacteria biofuels process which may be based on the synthetic symbiosis of bacteria by creating an energy shuttle through the use of nitrogenous species recycling, which may represent a transformational step to the biofuels industry. Biofuels can be produced from $CO_2$ sources using chemoautotrophic (CAT) bacteria such as those in the genera *Nitrosomonas, Nitrosococcus, Nitrobacter, Nitrococcus* and others and nitrogen reducing bacteria (NRB) such as *Paracoccus denitrificans, Thiobacillus denitrificans* and others to form biomass that can be converted to biofuels.

The products extracted from the NRB-CAT bacterial biomass may provide advantages for processing biofuels. Materials extracted from the biomass may contain lipids and may contain paraffin. Paraffin may be a high-valued component used for industrial purposes including synthesis of ozone inhibitors in rubbers and hot climate asphalt additives. If successful, the concept may leapfrog over today's ethanol and algae approaches perhaps due to its siting flexibility as well as accommodating large $CO_2$ sources due to favorable economics with carbon capture credits and its non-reliance on local, dispersed and small scale-sources of nutrients.

Embodiments of the present invention may have the potential to be transformational in that it may provide a new, highly efficient pathway for biofuels production options, that can be reduced the nation's dependence on both domestic and foreign oil perhaps by up to about 64 billion barrel crude equivalents annually and can be rapidly deployed. A CAT bacteria-based system may provide the transportation sector with 'drop-in' fuels, such as biodiesel, aviation fuel, and gasoline perhaps providing a leap forward in commercial deployment relative to algae. The uniqueness of the CAT bacterial process may occur in three areas—process, product, and integration with a $CO_2$ source.

Embodiments of the present invention may provide a CAT bacteria process which may employ a unique shuttling system based on nitrogenous species, which may be abundant. It may not use any expensive rare earth elements or perhaps even any organic redox shuttles. Unlike other bacteria-based systems that may use metal-containing solids, a CAT bacteria system may be liquid phase perhaps avoiding the complications of transfer of fine solids in (and between) reactors, which may allow superior mixing and bacteria growth. By replacing solid particle based electron shuttling systems with soluble gases the tendency for biofilm on the shuttle substrate may be eliminated.

In embodiments, a feature of a CAT bacteria concept may employ a dual reactor system with perhaps different bacteria and different conditions thereby allowing for optimization of each bacteria growth. A system can modify $CO_2$ conditions to meet reduced nitrogenous species production in a controlled manner to produce the optimum production of biomass.

Unlike photosynthesis-based biofuels production process, a CAT-based process may not be driven by photosynthesis. Unlike photosynthesis-based algae processes that may capture less or no $CO_2$ during low light conditions, thus perhaps complicating their integration with a variety of $CO_2$ sources, even with the use of artificial lighting, a CAT bacteria process may provide a controlled and perhaps even constant capture of $CO_2$ independent of lighting conditions, thus maximizing yield.

Bacteria can be harvested separately to produce biofuels that may meet industry specifications and may maximize the recovery of high value components, such as paraffin or together for lipid yield and biofuel production. CAT bacteria produced lipid yields may be comparable to algae and may be used in petroleum replacement products as well as biofuels such as biodiesel. The NRB bacteria can produce one quarter of its extractable mass as paraffins, which may have high value use in ozone proofing rubber and as a hot climate asphalt additive. Heterotrophic bacteria may have similar growth rates to algae, perhaps affording reasonable lipid yields.

The footprint of the CAT bacteria-based system may be projected to be lower than ethanol or open algae production systems (acres/ton of biomass) perhaps by a factor of about 50 compared to open pond algae production systems and a factor of about 10 compared with algae photobioreactors that require external lighting at significant operating costs perhaps resulting in less restriction on CAT siting.

A CAT bacteria-based concept can be produced in reasonably sized modules to meet varying sized $CO_2$ sources and may be compatible with commercially available lipid extraction and biodiesel production process, thereby allowing for rapid deployment.

Embodiments of the present invention may be self sufficient with respect to nutrients by converting a non-oil portion of a biomass into nutrients needed in the process. Other microbial processes that require external nutrient sources may be limited in scale due to the quantity of local nutrients available and the infrastructure cost to deliver it to the $CO_2$ source, perhaps restricting potential deployment sites.

In a CAT bacteria-based process, $CO_2$ can be selectively removed from the flue gas and any remaining flue gas, $CO_2$ and other flue gas species can be can be handled through existing plant stack and plant infrastructure (fans), affording easy retrofit.

Unlike open algae systems with high evaporative water losses, the embodiments of the present invention may employ recycling in an essentially closed loop. Makeup water can also be supplied by low rank coal upgrading processes or even by produced waters from the coalbed methane and oil and gas production.

The bacteria-based concept may be unique and may offer many attributes making it a transformational and market disrupting technology with rapid development and broad and rapid commercial deployment options.

The bioreactor media and gas conditions may impact the carbon assimilation rates of selected chemoautotrophs and these chemoautotrophs may impact the product composition related to biofuels and petroleum replacement products. Other process data needed may include bacteria/strains growth rates, extractable product characteristics, water quality treatment needs, and perhaps even baseline data for operation of bioreactors.

Species/strains of bacteria for use in the nitrogen reducing bioreactor and the chemoautotrophic $CO_2$ capture bioreactor may be determined experimentally based on process efficiencies of bacteria species known to perform the required assimilations. Bacteria evaluated for the reduction of nitrogenous species may include *Paracoccus denitrificans*, as well as species in the genera *Paracoccus, Thiobacillus, Micrococcus, Pseudomonas, Alkaligenes, Bacillus, Sulfurimonas, Thiomicrospira, Alicycliphilus*, and others. The chemoautotrophic bacteria evaluated for use in the $CO_2$ capture bioreactor may include species from the genera *Nitrosomonas, Nitrosococcus, Nitrobacter, Nitrococcus, Nitrospira, Nitrosolobus, Nitrospina, Nitrococcus, Nitrososphaera, Nitrosopumilus*, and others. Several available species are expected to be effective. Bacteria used in the process may or may not be genetically modified to enhance certain features of the process.

Different bacteria may be utilized in the various embodiments of the present invention. As a non-limiting example, perhaps when using a chemoautotraphic bacteria perhaps even with ammonifying bacteria (e.g., NH3→NO2, NO2→NO3, then NO3→NH3) and perhaps with nitrogen containing compound energy supply, CAT bacteria may include but is not limited to at least one of *Nitrosomonas, Nitrosococcus, Nitrosospira, Nitrosolobus, Pedobacter* or any microorganism that nitrifies NH3 to NO2, or any combination thereof, or even at least one of *Nitrobacter, Nitrococcus, Nitrospina, Nitrospira* or any microorganism that nitrifies NO2 to NO3, or any combination thereof. NRB bacteria may include but is not limited to *Bacilla, Campylobacter, Citrobacter, Clostridium, Desulfovibrio, Enterobacter, Erwinia, Escherichia, Klebsiella, Neisseria, Photobacterium, Proteus, Pseudomonas, Salmonella, Selenomonas, Serratia, Streptomyces, Veillonella, Vibrio, Wolinella* or any microorganisms that ammonifies, or any combination thereof, or the like.

With a NCAT system perhaps with denitrifying bacteria (e.g., NH3→NO2, NO2→NO3, then NO3→N2. Option of catalytically going from N2→NH3), CAT bacteria may include but is not limited to At least one of *Nitrosomonas, Nitrosococcus, Nitrosospira, Nitrosolobus, Pedobacter* or any microorganism that nitrifies NH3 to NO2, or combinations thereof; or even at least one of *Nitrobacter, Nitrococcus, Nitrospina, Nitrospira* or any microorganism that nitrifies NO2 to NO3, or combinations thereof. NRB bacteria may include but is not limited to *Alcaligenes, Agrobacterium, Aquaspirillum, Azospirillum, Bacissul, Blastobacter, Bradyrhizobium, Branhamella, Chromobacterium, Cytophaga, Flavobacterium, Flexibacter, Halobacterium, Hyphomicrobium, Kingella, Neisseria, Paracoccus, Propionibacterium, Pseudomonas, Rhizobium, Wolinella, Rhodopseudomonas, Thiobacillus, Thiomicrospira, Thiosphaera, Alicycliphilus, Kingella, Achromobacter, Micrococcus, Jonesia, Roseobacter, Shewanella, Sterolibacterium, Castellaniella, Comomonas, Paracoccus, Thiobacillus, Thiomicrospira, Thiosphaera* or other microorganisms that denitrify or combinations thereof or the like.

With CAT systems perhaps utilizing two inorganics, CAT bacteria (e.g., that use NH3 and NO2 (NH3→NO2, NO2→NO3)) may include but is not limited to at least one of *Nitrosomonas, Nitrosococcus, Nitrosospira, Nitrosolobus, Pedobacter* or any microorganism that nitrifies NH3 to NO2, or combinations thereof; or perhaps even at least one of *Nitrobacter, Nitrococcus, Nitrospina, Nitrospira* or any microorganism that nitrifies NO2 to NO3, or combinations thereof. CAT bacteria that oxidize nitrate perhaps while reducing sulfur (e.g., NO3→N2, S-2→SO4) may include but is not limited to *Paracoccus, Thiobacillus, Thiomicrospira, Thiosphaera*, or other microorganisms that reduce NO3 while oxidizing inorganic sulfur compounds, or combinations thereof or the like. SRB bacteria may include but is not limited to *Archeaoglobus, Caldivirga, Desulfarculus, Desulfobacteraceae, Desulfobacterium, Desulfobotulus, Desulfobulbaceae, Desulfobulbus, Desulfocaldus, Desulfofustis, Desulfohalobium, Desulfomicrobium, Desulfomonile, Desulfonatronum, Desulfonotronovibrio, Desulforhopalus, Desulfosporamusa, Desulfosporosinus, Desulfotomaculum, Desulfovacula, Desulfovibrio, Thermocladium, Thermodesulfatator, Thermodesulfobacterium, Thermodesulfobium, Thennodesulfovibrio*, or other microorganisms that reduce sulfate, or combinations thereof or the like.

Bioreactors may be used to culture the bacteria to determine perhaps the most prolific species for the capture of $CO_2$ and reactor sizing. Optimal conditions within the bioreactors can be determined for each bacteria/strain using a number of environmental variables. Process parameters may be controlled using computer systems equipped to maintain constant conditions and perhaps to identify small changes in biomass production. The impact of nutrient combinations and sources on bacteria populations and assimilations can also be determined.

Biomass may be harvested from the chemoautotrophic bioreactors at intervals near the peak in the growth phase of the bacteria. The impact of biomass removal on growth rate of the bacteria may be determined with the objective of establishing the optimum removal point that will not detract from the continued pace of $CO_2$ assimilation. $CO_2$ can be incorporated into the chemoautotrophic bioreactor using injection methods. The rate of $CO_2$ assimilation can be determined for each injection method evaluated. The maximum solution concentrations of $CO_2$ can be determined along with the corresponding rate of $CO_2$ assimilation.

The conventional method of harvesting the bacteria from the bioreactors may be by filtration, followed by a drying step, an oil extraction step and perhaps even the production of the biodiesel. It may be desirable to assess advanced technologies being developed by others as to their applicability to any core chemoautotrophic bacteria carbon capture and biofuels process. There may be a number of advanced harvesting techniques that are being developed for other biofuels and other industries that may have promise with the process of the embodiments of the present invention. Most harvesting methods available for microbial process may have been originally developed for animal tissues and plant materials. The development of harvesting processes may depend on the conditions of the culture media, nature of the bacteria cells, or perhaps even the type of extract desired. The following process steps may be examined: (1) killing or forced dormancy of the bacteria can be achieved by several approaches, including heating, cooling, foaming, addition of chemical agents such as acid, base, sodium hypochlorite, enzymes, or antibiotics; (2) the technologies available to separate the bacteria from the bulk culture media may involve centrifugation, rotary vacuum filtration, pressure filtration, hydrocycloning, flotation, skimming, and perhaps even sieving. These technologies can be applied in conjunction with other techniques, such as addition of flocculating agents, or coagulating agents. The relevant parameters to be determined may include bacteria size, density and tendency to coalesce into larger flocks; (3) water may need to be removed from the harvested bacteria to prevent the occurrence of lipolysis or perhaps even metabolically the breakdown of glycerides into free fatty acids within bacteria cells. Various technologies may be used for the drying step, such as perhaps direct and even indirect methods; and perhaps even (4) after dewatering, the lipids and fatty acids may be separated from the bacterial mass, or even extracted. It may be important during the extraction to prevent oxidative degradation and perhaps even to minimize the presence of artifacts to ensure high yield of glycerides. Available approaches may include but are not limited to centrifugation, high pressure homogenization, filtration, as well as solvents such as methanol or ethanol extraction. Solvent extraction can be a combination of mechanical and chemical cell lysis, or cell disruption. Mechanical methods of lysis as well as chemical methods and enzymes may also be employed.

Figure 5:
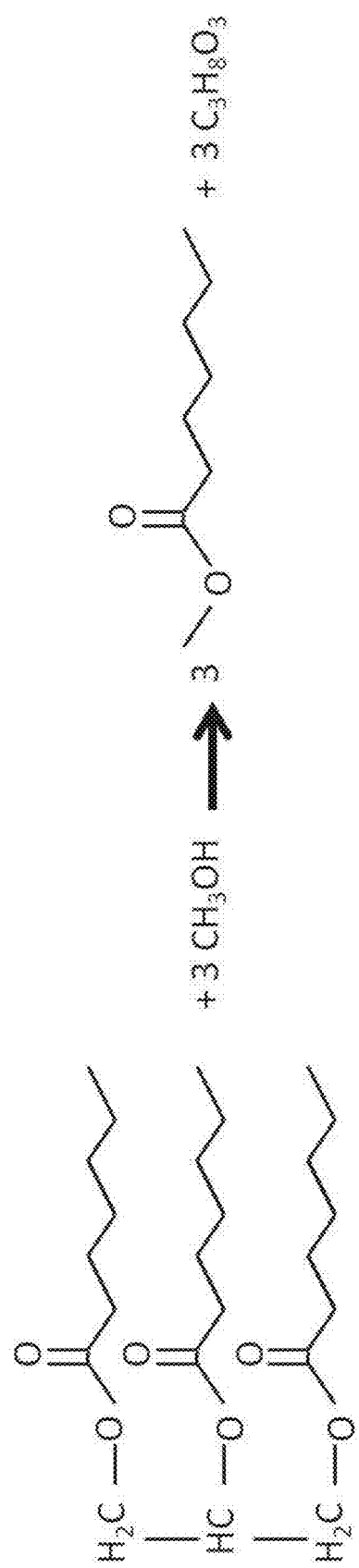
FIG. 5 is an example of catalytic transesterification of a triglyceride.

It may be desirable to assess the application of advanced technology for biodiesel production as well as other bioproducts, such as green plastics. From a chemical point of view, biodiesel may be mainly composed of fatty acids mono-alkyl esters. It may be produced from triglycerides (the major compounds of oils and fats) with short chain alcohols perhaps via catalytic transesterification as shown in the example of FIG. 5. Depending on the type of catalyst adopted, the methods for biodiesel production can be classified as conventional or perhaps even enzyme based. For the former, alkali catalysts, such as KOH and NaOH, with the combination of acid catalyst, such as phosphorus acid, may be used. For the latter, enzyme, such as lipase, may be used as catalyst. These techniques may be applicable to various embodiments of the present invention. Extracted microbial oil can also be used for the production of green plastics. The major component of the residue may be the cell debris leftover from oil and fatty acid extraction. Like algae, cell debris of the bacteria may contain cellulose and perhaps even a variety of glycoproteins. These components may be analyzed and evaluated for end use applications.

Various types of lipid materials, including paraffins and glycerides, can be produced by bacteria. In the bacteria harvesting, the glyceride, paraffinic, and other lipid materials from these processes may be produced. Glycerides may be transesterified with methanol (to perhaps biodiesel). Produced biodiesel for use as a transportation fuel need to follow ASTM method D6751.

Control of dual reactors and perhaps even the resultant products under continuous operation are important. These may represent critical items for commercial deployment. In addition, the operational issues such as fouling and perhaps even scaling may need to be known and resolved prior to commercial deployment.

Embodiments of the present invention may include a plant design, development and perhaps even validation may consist of integration of two bacteria bioreactors and verification of operational parameters. A system may be based on two independent bacterial systems perhaps providing essential sulfur looping to sustain carbon capture at a constant and predictable rate. It may be desirable to size, determine and optimize operational conditions perhaps to ensure efficient coupling of the systems within the operational regime. Bacterial species selection may be key in this effort, perhaps due to the highly specific needs of individual and consortium bacterial species. Design parameters may specify fluid stream flow rates and chemical composition for control of nutrient addition, pH, reduced nitrogenous species recovery and delivery systems, operational temperatures for the subsystem reactors, and perhaps even working volume for desired output parameters for each of the subsystems. Also, the system design may consider comparison of state-of-the-art membrane gas infusion techniques in comparison with traditional gas sparging. In addition, techniques developed for harvesting microalgae may be evaluated for bacteria, and may have to be modified accordingly.

Embodiments of the present invention may include but are not limited to vessel sizing, line sizing, input/output identification, system parameter monitoring specification, and perhaps even biomass density calculations. This may include design of reduced nitrogen species recovery units for the control of reduced nitrogen species levels in the primary nitrogen reducing reactor, and may even include delivery units for the infusing of reduced nitrogen species into the secondary carbon fixing reactor. Also, $CO_2$ species control through pH and monitoring of these species online and integrated into the control system may be designed. This may involve assigning process control steps to develop relationships between $CO_2$ uptake, carbon cycling in the reactor, reduced nitrogen species to $CO_2$ uptake, and perhaps even the best source reduction or increase to accomplish these reactions in a controlled manner while maximizing carbon conversion. Gas feed to the reaction vessels can be designed with the flexibility to evaluate multiple gas sparging and perhaps even membrane based gas infusion technologies. This may include comparison of existing technologies for extraction of oils from bacteria and perhaps even determination of the most suitable choice for the application, or the development of new technologies to tailor the extraction technique to bacterial applications.

The technology may leverage synthetic biology and metabolic engineering advances to modify microbiological metabolic pathways and perhaps even develop novel biological systems that can directly utilize electrons and reduced ions as a source of reducing equivalents for conversion of $CO_2$ to liquid fuels. In addition, the CAT process may be a specifically engineered system and set of bioreactors to provide an ecosystem environment that cultures bacterium and may be self-sustaining resulting in a robust organism engineered ecosystem well suited for commercial scale integration with carbon dioxide emitting facilities.

Clauses:

Clause 1. A method of biologically reducing carbon dioxide pollutants comprising the steps of:
containing at least some carbon dioxide emissions from a carbon dioxide emitter;
introducing at least some carbon dioxide emissions from said carbon dioxide emitter into at least one processing reactor;
chemoautotrophically digesting carbon dioxide of said at least some carbon dioxide emissions with a plurality of chemoautotrophic bacteria in said at least one processing reactor;
generating reduced sulfur containing compounds from sulfate reducing bacteria in a separate processing reactor;
supplying said sulfur containing compounds as an energy supply to said plurality of chemoautotrophic bacteria in said at least one processing reactor;
biologically producing at least some biomass from said chemoautotrophic digestion of said carbon dioxide with said chemoautotrophic bacteria;
ecologically reducing atmospheric release of said carbon dioxide emitted from said carbon dioxide emitter;
providing an acetate conversion reactor;
feeding acetate generated from said sulfate reducing bacteria into said acetate conversion reactor; and
generating biomass from said acetate conversion reactor.

Clause 2. A method of biologically reducing carbon dioxide pollutants comprising the steps of:
containing at least some carbon dioxide emissions from a carbon dioxide emitter;
introducing at least some carbon dioxide emissions from said carbon dioxide emitter into at least one processing reactor;
chemoautotrophically digesting carbon dioxide of said at least some carbon dioxide emissions with a plurality of chemoautotrophic bacteria in said at least one processing reactor;
providing a nitrogenous compound energy supply to said plurality of chemoautotrophic bacteria in said at least one processing reactor;
biologically producing at least some biomass from said chemoautotrophic digestion of said carbon dioxide with said chemoautotrophic bacteria; and
ecologically reducing atmospheric release of said carbon dioxide emitted from said carbon dioxide emitter.

Clause 3. A method of biologically reducing carbon dioxide pollutants according to Clause 1 or 2 or any other clause wherein said step of containing said at least some carbon dioxide emissions from said carbon dioxide emitter comprises the step of containing up to about 100% of said at least some carbon dioxide emissions from said carbon dioxide emitter.

Clause 4. A method of biologically reducing carbon dioxide pollutants according to Clause 1 or 2 or any other clause wherein said industrial carbon dioxide emitter is selected from a group consisting of power generation sources, mining operations, municipal waste landfills, cement producing plants, lime producing plants, coal refineries, oil refineries, refineries, trona processing plants, Fischer-Tropsch synthesis plants, coal-to-liquids plants, gas-to-liquids plants, biomass-to-liquids plants, gasification facilities, non-power generation sources, coal-fired power plants, natural gas-fired power plants, fuel cells, and combustion power plants.

Clause 5. A method of biologically reducing carbon dioxide pollutants according to Clause 2 or any other clause wherein said chemoautotrophic bacteria are selected from a group consisting of the genera *Nitrosomonas, Nitrosococcus, Nitrosospira, Nitrosolobus, Pedobacter, Nitrobacter, Nitrococcus, Nitrospina*, any bacteria that naturally nitrifies, and combinations thereof.

Clause 6. A method of biologically reducing carbon dioxide pollutants according to Clause 1 or 2 or any other clause wherein said chemoautotrophic bacteria comprises genetically engineered chemoautotrophic bacteria for nitrification.

Clause 7. A method of biologically reducing carbon dioxide pollutants according to Clause 2 or any other clause wherein said nitrogenous compound energy supply comprises a reduced nitrogenous compound energy supply to said plurality of chemoautotrophic bacteria.

Clause 8. A method of biologically reducing carbon dioxide pollutants according to Clause 7 or any other clause wherein said reduced nitrogenous compound energy supply is selected from a group consisting of ammonia and ammonium.

Clause 9. A method of biologically reducing carbon dioxide pollutants according to Clause 7 or any other clause wherein said reduced nitrogenous compound energy supply comprises nitrite.

Clause 10. A method of biologically reducing carbon dioxide pollutants according to Clause 2 or any other clause wherein said step of providing said nitrogenous compound energy supply to said plurality of chemoautotrophic bacteria comprises the step of recycling said nitrogenous compound energy supply to said plurality of chemoautotrophic bacteria in said at least one processing reactor.

Clause 11. A method of biologically reducing carbon dioxide pollutants according to Clause 10 or any other clause wherein said step of recycling said nitrogenous compound energy supply to said chemoautotrophic bacteria in said at least one processing reactor comprises the step of recycling said nitrogenous compound energy supply from at least one additional processing reactor.

Clause 12. A method of biologically reducing carbon dioxide pollutants according to Clause 11 or any other clause and further comprising the steps of generating said nitrogenous compound energy supply in said at least one additional processing reactor and supplying said nitrogenous compound energy supply to said at least one processing reactor containing said plurality of chemoautotrophic bacteria.

Clause 13. A method of biologically reducing carbon dioxide pollutants according to Clause 10 or 12 or any other clause and further comprising the steps of:
 providing a plurality of ammonifying bacteria in said at least one additional processing reactor;
 connecting said at least one processing reactor containing said plurality of chemoautotrophic bacteria to said at least one additional processing reactor containing said ammonifying bacteria;
 generating nitrate in said at least one processing reactor containing said chemoautotrophic bacteria;
 supplying said nitrate from said at least one processing reactor containing said chemoautotrophic bacteria to said at least one additional processing reactor containing said ammonifying bacteria;
 generating ammonia or ammonium in said at least one additional processing reactor containing said ammonifying bacteria; and
 supplying said ammonia or ammonium from said at least one additional processing reactor containing said ammonifying bacteria to said at least one processing reactor with said plurality of chemoautotrophic bacteria.

Clause 14. A method of biologically reducing carbon dioxide pollutants according to Clause 2 or any other clause and further comprising the step of providing ammonifying bacteria in said at least one processing reactor.

Clause 15. A method of biologically reducing carbon dioxide pollutants according to Clause 14 or any other clause and further comprising the step of providing an energy supply to said ammonifying bacteria in said at least one processing reactor.

Clause 16. A method of biologically reducing carbon dioxide pollutants according to Clause 15 or any other clause wherein said step of providing said energy supply to said ammonifying bacteria comprises the step of providing organic carbon to said ammonifying bacteria.

Clause 17. A method of biologically reducing carbon dioxide pollutants according to Clause 13 or 14 or any other clause wherein said ammonifying bacteria is selected from a group consisting of: *Bacillus, Campylobacter, Citrobacter, Clostridium, Desulfovibrio, Enterobacter, Erwinia, Escherichia, Klebsiella, Neisseria, Photobacterium, Proteus, Pseudomonas, Salmonella, Selenomonas, Serratia, Streptomyces, Veillonella, Vibrio, Wolinella*, any bacteria that ammonify, and any combination thereof.

Clause 18. A method of biologically reducing carbon dioxide pollutants according to Clause 3 or any other clause wherein said plurality of said chemoautotrophic bacteria is selected from a group consisting of: *Nitrosomonas, Nitrosococcus, Nitrosospira, Nitrosolobus, Pedobacter, Nitrobacter, Nitrococcus, Nitrospina, Nitrospira*, and any combination thereof.

Clause 19. A method of biologically reducing carbon dioxide pollutants according to Clause 18 or any other clause wherein said plurality of said chemoautotrophic bacteria comprises at least one bacteria selected from a group consisting of *Nitrosomonas, Nitrosococcus, Nitrosospira, Nitrosolobus, Pedobacter*, and at least one additional bacteria selected from a group consisting of *Nitrobacter, Nitrococcus, Nitrospina, Nitrospira*.

Clause 20. A method of reducing carbon dioxide pollutants according to Clause 13 or 14 or any other clause and further comprising the step of providing recycled process biomass residue as an electron donor supply to said ammonifying bacteria.

Clause 21. A method of biologically reducing carbon dioxide pollutants according to Clause 11 or any other clause and further comprising the steps of:
 providing a plurality of denitrifying bacteria in said at least one additional processing reactor;
 connecting said at least one processing reactor containing said plurality of chemoautotrophic bacteria to said at least one additional processing reactor containing said denitrifying bacteria;
 generating an element selected from a group consisting of nitrate, nitrite, and a combination thereof in said at least one processing reactor containing said chemoautotrophic bacteria;
 supplying said element from said at least one processing reactor containing said chemoautotrophic bacteria to said at least one additional processing reactor containing said denitrifying bacteria;
 generating nitrogen in said at least one additional processing reactor containing said denitrifying bacteria;
 reacting said nitrogen produced in said denitrifying reactor in a chemical process to produce ammonia; and
 supplying said ammonia from said chemical process to said at least one processing reactor containing said plurality of chemoautotrophic bacteria.

Clause 22. A method of biologically reducing carbon dioxide pollutants according to Clause 2 or any other clause wherein said step of providing said nitrogenous compound energy supply to said plurality of chemoautotrophic bacteria comprises the step of supplying said nitrogenous compound energy supply from a catalytic process reaction.

Clause 23. A method of biologically reducing carbon dioxide pollutants according to Clause 22 or any other clause wherein said catalytic process is the Haber process.

Clause 24. A method of biologically reducing carbon dioxide pollutants according to Clause 2 or any other clause and further comprising the step of providing denitrifying bacteria in said at least one processing reactor.

Clause 25. A method of biologically reducing carbon dioxide pollutants according to Clause 24 or any other clause and further comprising the step of providing an energy supply to said denitrifying bacteria in said at least one processing reactor.

Clause 26. A method of biologically reducing carbon dioxide pollutants according to Clause 25 or any other clause wherein said step of providing said energy supply to said denitrifying bacteria comprises the step of providing organic carbon to said denitrifying bacteria.

Clause 27. A method of biologically reducing carbon dioxide pollutants according to Clause 21 or 22 or any other clause wherein said denitrifying bacteria is selected from a group consisting of: *Alcaligenes, Agrobacterium, Aquaspirillum, Azospirillum, Bacillus, Blastobacter, Bradyrhizobium, Branhamella, Chromobacterium, Cytophaga, Flavobacterium, Flexibacter, Halobacterium, Hyphomicrobium, Kingella, Neisseria, Paracoccus, Propionibacterium, Pseudomonas, Rhizobium, Wolinella, Rhodopseudomonas, Thiobacillus, Thiomicrospira, Thiosphaera, Alicycliphilus, Kingella, Achromobacter, Micrococcus, Jonesia, Roseobacter, Shewanella, Sterolibacterium, Castellaniella, Comomonas, Paracoccus, Thiobacillus, Thiomicrospira, Thiosphaera*, and any combination thereof.

Clause 28. A method of biologically reducing carbon dioxide pollutants according to Clause 21 or 22 or any other clause and further comprising the step of providing recycled process biomass residue as an electron donor supply to said denitrifying bacteria.

Clause 29. A method of biologically reducing carbon dioxide pollutants according to Clause 2 or any other clause and further comprising the steps of:
supplying an ammonia element selected from a group consisting of ammonia, ammonium, ammonia nitrate, and any combination thereof to said at least one processing reactor;
connecting said at least one processing reactor containing said plurality of chemoautotrophic bacteria to a second processing reactor containing a plurality of denitrifying bacteria;
generating an element selected from a group consisting of nitrate, nitrite, or a combination thereof in said at least one processing reactor containing said plurality of chemoautotrophic bacteria;
supplying said element from said at least one processing reactor containing said plurality of chemoautotrophic bacteria to said second processing reactor containing said plurality of denitrifying bacteria;
producing nitrogen in said second processing reactor containing said plurality of denitrifying bacteria; and
releasing said produced nitrogen.

Clause 30. A method of biologically reducing carbon dioxide pollutants according to Clause 29 or any other clause and further comprising the step of providing an energy supply to said denitrifying bacteria in said at least one processing reactor.

Clause 31. A method of biologically reducing carbon dioxide pollutants according to Clause 30 or any other clause wherein said step of providing said energy supply to said denitrifying bacteria comprises the step of providing organic carbon to said denitrifying bacteria.

Clause 32. A method of biologically reducing carbon dioxide pollutants according to Clause 29 or any other clause wherein said denitrifying bacteria is selected from a group consisting of: *Alcaligenes, Agrobacterium, Aquaspirillum, Azospirillum, Bacillus, Blastobacter, Bradyrhizobium, Branhamella, Chromobacterium, Cytophaga, Flavobacterium, Flexibacter, Halobacterium, Hyphomicrobium, Kingella, Neisseria, Paracoccus, Propionibacterium, Pseudomonas, Rhizobium, Wolinella, Rhodopseudomonas, Thiobacillus, Thiomicrospira, Thiosphaera, Alicycliphilus, Kingella, Achromobacter, Micrococcus, Jonesia, Roseobacter, Shewanella, Sterolibacterium, Castellaniella, Comomonas, Paracoccus, Thiobacillus, Thiomicrospira, Thiosphaera*, and any combination thereof.

Clause 33. A method of biologically reducing carbon dioxide pollutants according to Clause 29 or any other clause and further comprising the step of providing recycled process biomass residue as an electron donor supply to said denitrifying bacteria.

Clause 34. A method of biologically reducing carbon dioxide pollutants according to Clause 11 or any other clause and further comprising the steps of:
providing a plurality of nitrate reducing bacteria in said at least one additional processing reactor;
connecting said at least one processing reactor containing said plurality of chemoautotrophic bacteria to said at least one additional processing reactor containing said plurality of nitrate reducing bacteria;
generating nitrate in said at least one processing reactor containing said chemoautotrophic bacteria;
supplying said nitrate from said at least one processing reactor containing said plurality of chemoautotrophic bacteria to said at least one additional processing reactor containing said plurality of nitrate reducing bacteria;
generating nitrite in said at least one additional processing reactor containing said plurality of nitrate reducing bacteria; and
supplying said nitrite from said at least one additional processing reactor containing said plurality of nitrate reducing bacteria to said at least one processing reactor with said plurality of chemoautotrophic bacteria.

Clause 35. A method of biologically reducing carbon dioxide pollutants according to Clause 2 or any other clause wherein said step of providing said energy supply to said plurality of chemoautotrophic bacteria comprises the step of providing nitrite ions or nitrite containing compounds to said plurality of chemoautotrophic bacteria.

Clause 36. A method of biologically reducing carbon dioxide pollutants according to Clause 35 or any other clause wherein said step of providing said nitrite ions or nitrite containing compounds to said plurality of chemoautotrophic bacteria comprises the step of supplying said nitrite ions or nitrite containing compounds from at least one additional processing reactor containing nitrate reducing bacteria.

Clause 37. A method of biologically reducing carbon dioxide pollutants according to Clause 2 or any other clause and further comprising the step of providing a plurality of nitrate reducing bacteria in said at least one processing reactor.

Clause 38. A method of biologically reducing carbon dioxide pollutants according to Clause 37 or any other clause and further comprising the step of providing an energy supply to said nitrate reducing bacteria in said at least one processing reactor.

Clause 39. A method of biologically reducing carbon dioxide pollutants according to Clause 38 or any other clause wherein said step of providing said energy supply to said nitrate reducing bacteria comprises the step of providing organic carbon to said nitrate reducing bacteria.

Clause 40. A method of biologically reducing carbon dioxide pollutants according to Clause 34 or 37 or any other clause wherein said nitrate reducing bacteria is selected from a group consisting of *Alcaligenes, Agrobacterium, Aquaspirillum, Azospirillum, Bacissul, Blastobacter, Bradyrhizobium, Branhamella, Chromobacterium, Cytophaga, Flavobacterium, Flexibacter, Halobacterium, Hyphomicrobium, Kingella, Neisseria, Paracoccus, Propionibacterium, Pseudomonas, Rhizobium, Wolinella, Rhodopseudomonas, Thiobacillus, Thiomicrospira, Thiosphaera, Alicycliphilus, Kingella, Achromobacter, Micrococcus, Jonesia, Roseobacter, Shewanella, Sterolibacterium, Castellaniella, Comomonas, Paracoccus, Thiobacillus, Thiomicrospira, Thiosphaera*, and any combination thereof.

Clause 41. A method of biologically reducing carbon dioxide pollutants according to Clause 34 or 37 or any other clause and further comprising the step of providing recycled process biomass residue as an electron donor supply to said nitrate reducing bacteria.

Clause 42. A method of biologically reducing carbon dioxide pollutants according to Clause 11 or any other clause and further comprising the steps of:
providing a plurality of denitrifying bacteria in said at least one additional processing reactor;
connecting said at least one processing reactor containing said plurality of chemoautotrophic bacteria to said at least one additional processing reactor containing said denitrifying bacteria;
generating an element selected from a group consisting of nitrate, nitrite, or a combination thereof in said at least one processing reactor containing said plurality of chemoautotrophic bacteria;
supplying said element from said at least one processing reactor containing said plurality of chemoautotrophic bacteria to said at least one additional processing reactor containing said denitrifying bacteria;
producing nitrogen in said at least one additional processing reactor containing said plurality of denitrifying bacteria; and
releasing said produced nitrogen.

Clause 43. A method of biologically reducing carbon dioxide pollutants according to claim 42 or any other clause and further comprising the step of feeding fertilizer into said at least one additional processing reactor containing said chemoautotrophic bacteria.

Clause 44. A method of biologically reducing carbon dioxide pollutants according to Clause 11 or any other clause and further comprising the steps of:
providing a plurality of nitrate reducing bacteria in said at least one additional processing reactor;
generating nitrite in said at least one additional processing reactor containing said plurality of nitrate reducing bacteria;
supplying said nitrite from said at least one additional processing reactor containing said plurality of nitrate reducing bacteria to said at least one processing reactor with said plurality of chemoautotrophic bacteria;
providing an acetate conversion reactor;
feeding acetate generated from said nitrate reducing bacteria into said acetate conversion reactor; and
generating biomass from said acetate conversion reactor.

Clause 45. A method of biologically reducing carbon dioxide pollutants according to Clause 44 or any other clause and further comprising the step of feeding acetate generated from nutrient production into said acetate conversion reactor.

Clause 46. A method of biologically reducing carbon dioxide pollutants comprising the steps of:
containing at least some carbon dioxide emissions from a carbon dioxide emitter;
introducing at least some carbon dioxide emissions from said carbon dioxide emitter into at least one processing reactor;
chemoautotrophically digesting carbon dioxide of said at least some carbon dioxide emissions with a plurality of chemoautotrophic bacteria in said at least one processing reactor;
providing a plurality of sulfur reducing bacteria;
providing a plurality of sulfur oxidizing nitrate reducing bacteria;
biologically producing at least some biomass from said chemoautotrophic digestion of said carbon dioxide with said chemoautotrophic bacteria; and
ecologically reducing atmospheric release of said carbon dioxide emitted from said industrial carbon dioxide emitter.

Clause 47. A method of biologically reducing carbon dioxide pollutants according to Clause 46 or any other clause and further comprising the steps of:
generating nitrate in said at least one processing reactor containing said plurality of chemoautotrophic bacteria;
feeding said nitrate to said plurality of sulfur oxidizing nitrate reducing bacteria;
generating sulfate from said plurality of sulfur oxidizing nitrate reducing bacteria;
feeding said sulfate from said plurality of sulfur oxidizing nitrate reducing bacteria to said sulfur reducing bacteria;
generating sulfide from said plurality of sulfur reducing bacteria; and
feeding said sulfide to said sulfur oxidizing nitrate reducing bacteria.

Clause 48. A method of biologically reducing carbon dioxide pollutants according to Clause 47 or any other clause and further comprising the steps of:
generating nitrogen from said plurality of sulfur oxidizing nitrate reducing bacteria Clause 49. A method of biologically reducing carbon dioxide pollutants according to Clause 47 or any other clause and further comprising the steps of:
reacting said nitrogen to produce ammonia; and
feeding said ammonia to said plurality of chemoautotrophic bacteria in said at least one processing reactor.

Clause 50. A method of biologically reducing carbon dioxide pollutants according to Clause 46 or any other clause and further comprising the steps of providing at least one additional processing reactor.

Clause 51. A method of biologically reducing carbon dioxide pollutants according to Clause 50 wherein said at least one additional processing reactor contains bacteria selected from a group consisting of said plurality of sulfur reducing bacteria, said plurality of nitrogen reducing bacteria, and a combination thereof.

Clause 52. A method of biologically reducing carbon dioxide pollutants according to Clause 46 or any other clause wherein said nitrogen reducing bacteria comprises denitrifying bacteria.

Clause 53. A method of biologically reducing carbon dioxide pollutants according to Clause 46 or any other clause and further comprising the step of supplying ammonia or ammonium to said plurality of chemoautotrophic bacteria in said at least one processing reactor.

Clause 54. A method of biologically reducing carbon dioxide pollutants according to Clause 1 or any other clause wherein said chemoautotrophic bacteria are selected from a group consisting of the genera *Thiobacillus, Paracoccus, Thiovulum, Thiomicrospira*, any bacteria that oxidize inorganic sulfur during chemoautotrophic growth, and combinations thereof.

Clause 55. A method of biologically reducing carbon dioxide pollutants according to Clause 46 or any other clause and further comprising a processing reactor for each of said bacteria.

Clause 56. A processing system for biological reduction of carbon dioxide pollutants comprising:
at least one processing reactor configured to receive said at least some carbon dioxide emissions from an industrial carbon dioxide emitter;
a plurality of chemoautotrophic bacteria in said at least one processing reactor configured to digest at least some of said carbon dioxide;
an amount of biologically produced biomass by said chemoautotrophic bacteria located in said at least one processing reactor;
an ecological reduction of atmospheric release of said carbon dioxide emissions;
sulfur containing compounds generated by sulfate reducing bacteria;
a supply of said sulfur containing compounds to said chemoautotrophic bacteria located in said at least one processing reactor;
an acetate conversion reactor;
acetate generated from said sulfate reducing bacteria;
a feed supply of said acetate from said sulfate reducing bacteria to said acetate conversion reactor; and
biomass generated from said acetate conversion reactor.

Clause 57. A processing system for biological reduction of carbon dioxide pollutants comprising:
at least one processing reactor configured to receive said at least some carbon dioxide emissions from an industrial carbon dioxide emitter;
a plurality of chemoautotrophic bacteria in said at least one processing reactor configured to digest at least some of said carbon dioxide;
an amount of biologically produced biomass by said chemoautotrophic bacteria located in said at least one processing reactor;
an ecological reduction of atmospheric release of said carbon dioxide emissions;
nitrogen containing compounds generated by bacteria;
a feed supply of said nitrogen containing compounds to said chemoautotrophic bacteria located in said at least one processing reactor;

Clause 58. A processing system for biological reduction of carbon dioxide pollutants according to Clause 57 or any other clause and further comprising:
an acetate conversion reactor;
acetate generated from said sulfate reducing bacteria;
a feed supply of said acetate from said nitrogen reducing bacteria to said acetate conversion reactor; and
biomass generated from said acetate conversion reactor.

Clause 59. A processing system for biological reduction of carbon dioxide pollutants according to Clause 57 or any other clause and further comprising:
a nutrient production element;
acetate generated from said nutrient production element; and
a feed supply of said acetate from said nutrient production element to said acetate conversion reactor Clause 60. A processing system for biological reduction of carbon dioxide pollutants according to Clause 57 or any other clause wherein said bacteria comprises ammonifying bacteria.

Clause 61. A processing system for biological reduction of carbon dioxide pollutants according to Clause 57 or any other clause wherein said bacteria comprises denitrification bacteria.

Clause 62. A processing system for biological reduction of carbon dioxide pollutants according to Clause 57 or any other clause wherein said bacteria is located in at least one additional processing reactor.

Clause 63. A processing system for biological reduction of carbon dioxide pollutants according to Clause 57 or any other clause and further comprising:
nitrate generated by said plurality of chemoautotrophic bacteria in said at least one processing reactor; and
a feed supply of said nitrate to said bacteria.

Clause 64. A processing system for biological reduction of carbon dioxide pollutants comprising:
at least one processing reactor configured to receive said at least some carbon dioxide emissions from an industrial carbon dioxide emitter;
a plurality of chemoautotrophic bacteria in said at least one processing reactor configured to digest at least some of said carbon dioxide;
a plurality of sulfur reducing bacteria in at least one additional processing reactor;
a plurality of plurality of nitrogen reducing bacteria in said at least one additional processing reactor;
an amount of biologically produced biomass by said chemoautotrophic bacteria located in said at least one processing reactor;
an ecological reduction of atmospheric release of said carbon dioxide emissions; and
nitrogen containing compounds generated by bacteria;

Clause 65. A processing system for biological reduction of carbon dioxide pollutants according to Clause 64 or any other clause further comprising:
nitrate generated by said plurality of chemoautotrophic bacteria;
a feed supply of said nitrate to said plurality of nitrate reducing bacteria;
sulfate generated from said plurality of nitrate reducing bacteria;
a feed supply of said sulfate from said plurality of nitrate reducing bacteria to said sulfur reducing bacteria;
sulfite generated from said plurality of sulfur reducing bacteria; and
a feed supply of said sulfite to said nitrate reducing bacteria.

Clause 66. A processing system for biological reduction of carbon dioxide pollutants according to Clause 65 or any other clause and further comprising:

nitrogen generated from said plurality of nitrate reducing bacteria.

Clause 67. A processing system for biological reduction of carbon dioxide pollutants according to Clause 66 or any other clause and further comprising:
a nitrogen to ammonia conversion element; and
a feed supply of said ammonia to said plurality of chemoautotrophic bacteria in said at least one processing reactor.

Clause 68. A processing system for biological reduction of carbon dioxide pollutants according to Clause 65 or any other clause and further comprising: providing at least one additional processing reactor.

Clause 69. A processing system for biological reduction of carbon dioxide pollutants according to Clause 68 or any other clause wherein said at least one additional processing reactor contains bacteria selected from a group consisting of said plurality of sulfur reducing bacteria, said plurality of nitrogen reducing bacteria, and a combination thereof.

Clause 70. A processing system for biological reduction of carbon dioxide pollutants according to Clause 65 or any other clause wherein said nitrogen reducing bacteria comprises denitrifying bacteria.

Clause 71. A processing system for biological reduction of carbon dioxide pollutants according to Clause 62 or any other clause and further comprising a feed supply of ammonia or ammonium to said plurality of chemoautotrophic bacteria in said at least one processing reactor. As can be easily understood from the foregoing, the basic concepts of the present invention may be embodied in a variety of ways. It involves both biological conversion techniques as well as devices to accomplish the appropriate biological converter. In this application, the biological conversion techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "reactor" should be understood to encompass disclosure of the act of "reacting"—whether explicitly discussed or not—and, conversely, were there effectively disclosure of the act of "reacting", such a disclosure should be understood to encompass disclosure of a "reactor" and even a "means for reacting." Such changes and alternative terms are to be understood to be explicitly included in the description.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed below or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

I. U.S. Patent Documents

| Pat. No. | Kind Code | Issue Date | Name of Patentee or Applicant of cited Document |
|---|---|---|---|
| 8,349,587 | B2 | 2013 Jan. 8 | Fischer et al. |
| 5,981,266 | | 1999 Nov. 9 | Srivastava et al. |
| 8,478,444 | B2 | 2013 Jul. 2 | Fuxman et al. |
| 4,760,027 | | 1988 Jul. 26 | Sublette |
| 5,914,441 | | 1999 Jun. 22 | Hunter et al. |
| 5,173,429 | | 1992 Dec. 22 | Gaddy et al. |
| 5,593,886 | | 1997 Jan. 14 | Gaddy |
| 7,285,402 | B2 | 2007 Oct. 23 | Gaddy et al. |

II. U.S. Patent Application Publications

| Publication Number | Kind Code | Publication Date | Name of Patentee or Applicant of cited Document |
|---|---|---|---|
| 20080102515 | A1 | 2008 May 1 | Morales Cerda et al. |
| 20110287497 | A1 | 2011 Nov. 24 | Holtzapple et al. |
| 20130089899 | A1 | 2013 Apr. 11 | Kurek et al. |
| 20130189763 | A1 | 2013 Jul. 25 | Dalla-Betta et al. |
| 20130065285 | A1 | 2013 Mar. 14 | Sefton |
| 20130149755 | A1 | 2013 Jun. 13 | Reed et al. |
| 20130078690 | A1 | 2013 Mar. 28 | Reed |
| 20120085705 | A1 | 2012 Apr. 12 | Theodore et al. |
| 20130130341 | A1 | 2013 May 23 | Liao et al. |
| 20100120104 | A1 | 2010 May 13 | Reed |
| 20030002236 | A1 | 2003 Jan. 30 | Parent et al. |
| 20030066322 | A1 | 2003 Apr. 10 | Perriello |
| 20120003705 | A1 | 2012 Jan. 5 | Jin et al. |
| 20130189739 | A1 | 2013 Jul. 25 | Jin et al |

III. Foreign Patent Documents

| Foreign Document Number | Country Code | Kind Code | Publication Date | Name of Patentee or Applicant of cited Document |
|---|---|---|---|---|
| 2013006912 | WO | A1 | 2013 Jan. 17 | Bellamy |
| 2013148348 | WO | A1 | 2013 Oct. 3 | Kurek et al. |
| 2013082309 | WO | A1 | 2013 Jun. 6 | Reed et al. |
| 2011149956 | WO | A2 | 2011 Dec. 1 | Angotti et al. |
| 9118661 | WO | | 1991 Dec. 12 | Sublette |
| 2013074371 | WO | A2 | 2013 May 23 | Yeh et al. |
| 2008040365 | WO | A1 | 2008 Apr. 10 | Vanatalu et al. |
| 2011014507 | WO | A1 | 2011 Feb. 3 | The University of Wyoming Research Corporation |
| 2009002772 | WO | A1 | 2008 Dec. 31 | Algaedyne Corporation |
| 0218958 | EP | A2 | 1987 Apr. 22 | Combustion Engineering, Inc. |
| 2007109066 | WO | A1 | 2007 Sep. 27 | Petroalgae, LLC |
| 2011056183 | WO | A1 | 2011 May 12 | Sequesco |
| 2008128331 | WO | A1 | 2008 Oct. 30 | University Technologies International |

IV. Non-Patent Literature Documents

Akoh, C. C., S. Chang, G. Lee and J. Shaw, "Enzymatic approach to biodiesel production," J. Agric. Food Chem., 55, 8995-9005, 2007.

Antoni, D., V. V. Zverlov, and W. H. Schwarz, "Biofuels from microbes," Appl. Microbiol. Biot., 77, 23-35, 2007.

Bland, A., J. Newcomer, T. Zhang, K. Sellakumar, "Pilot testing of WRI's novel mercury control technology by pre-combustion thermal treatment of coal", Report to U.S. Department of Energy, Contract No. DE-FC26-98FT40323 Task 79, June 2009.

Certick, M. and S. Shimizu, "Review: biosynthesis and regulation of microbial polyunsaturated fatty acid production," J. Biosci. Bioeng., 87, 1-14, 1999.

Certik, M. and R. Horenitzky, "Supercritical CO2 extraction of fungal oil containing -linolenic acid," Biotechnol. Tech., 13, 11-15, 1999.

Chen, G., "A microbial polyhydroxyalkanoates (PHA) based bio- and materials industry," Chem. Soc. Rev., 38, 2434-2446, 2009.

Ciferno, J., "Pulverized coal oxycombustion power plants - final results" (revised), U.S. Department of Energy, National Energy Technology Laboratory, Nov. 1, 2007.

Cooney, M. J., E. Roschi, I. W. Marison, C. Comninellis, and U. Von Stockar, "Physiologic studies with the sulfate-reducing bacterium Desulfovibrio desulfuricans: Evaluation for use in a biofuel cell," Enzym. Microb. Tech., 8, 358-365, 1996.

Dasu, B. N., and K. L. Sublette, "Microbial Removal of sulfur dioxide from a gas stream with net oxidation to sulfate," Appl. Biochem. Biotech., Vol 20/21, 207-220, 1989.

Davis, J. B., "Paraffinic hydrocarbons in the sulfate reducing bacterium desulfovibrio desulfuricans," Chem. Geol., 3, 155-160, 1968.

Demirbas, Ayhan, "Sustainable cofiring of biomass with coal," Energy Conversion and Management, Vol 44, 1465-1479

Dhar, B. R., and K. Kirtania, "Excess methanol recovery in biodiesel production process using a distillation column: a simulation study," Chemical Engineering Research Bulletin, 13, 45-50, 2009.

DOE/NETL, "Cost and performance baseline for fossil energy plants-Vol. 1: bituminous coal and natural gas to electricity," DOE/NETL-2007/1281, May 2007, Revision 1, August 2007.

Garces, R., Alvarez-Ortega, R., Martinez-Force, E., S. Cantisan, "Lipid characterization in vegetative tissues of high saturated fatty acid sunflower mutants," J. Agric. Food Chem., 47, 78-82, 1999.

Green Econometrics, "Understanding the cost of solar energy," http://greenecon.net/understanding-the-cost-of-solar-energy/energy_economics.html, 2007.

GTM Research, "Transitioning from 1st generation to advanced biofuels," a white paper from Enterprise Florida and GTM Research, February 2010.

Howard, E. E., "Systems and methods for large-scale production and harvesting of oil-rich algae," PCT/US2007/006466, WO2007/109066 A1.

Kadam, K. L., "Environmental implications of power generation via coal-microalgae cofiring," Energy, Vol 27, 905-922, 2002.

Kelly, D. P, "Thermodynamic aspects of energy conservation by chemolithotrophic sulfur bacteria in relation to the sulfur oxidation pathways," Arch Microbial, 171, 219-229, 1999

Li, Q., W. Du, and D. Liu, "Perspectives of microbial oils for biodiesel production," Appl. Microbiol. Biot., 80, 749-756, 2008.

Mona, K. G., H. O. Sanaa, and M. A. Linda, "Single cell oil production by *Gordonia* spp. DG using agro-industrial wastes," World J. Microbiol. Biotechnol., 24, 1703-1711, 2008.

Monteiro, M. R., A. R. P. Ambrozin, L. M. Lião, and A. G. Ferreira, "Critical review on analytical methods for biodiesel characterization," Talanta, 77, 593-605, 2008, Parawira, W., "Biotechnological production of biodiesel fuel using biocatalysed transesterification: A review," Cr. Rev. Biotechn., 29, 82-93, 2009.

Rabus, R., T. A. Hansen and F. Widdel, "Dissimilatory sulfate- and sulfur-reducing prokaryotes," Prokaryotes, 2, 659-768, 2006.

Scott, K. M., and C. M. Cavanaugh, "CO2 uptake and fixation by endosymbiotic chemoautotrophs from the bivalve Solemya velum," Appl. Environ. Microb., 73, 1174-1179, 2007.

Shively, J. M., G. van Keulen, and W. G. Meijer, "Something from almost nothing: carbon dioxide fixation in chemoautotrophs," Annu. Rev. Microbiol, 52, 191-230, 1998.

Thurmond, W., Algae 2020: Algal Biofuels Demand Drivers, Players, Business Models, Markets & Commercialization Outlook, 1st edition, 2009, www.emerging-market.com.

van Lier, R. J. M., C. J. N. Buisman, and N. L. Piret, "THIOPAQ ® technology: versatile high-rate biotechnology for the mining and metallurgical industries," Proceedings of the TMS Fall Extraction and Processing Conference, v 3, p 2319-2328, 1999.

Yuan, W., A. C. Hansen, and Q. Zhang, "Predicting the physical properties of biodiesel for combustion modeling," T. ASAE, 46, 1487-1493, 2003.

Zhang, T., and L. T. Fan, "Significance of dead-state-based thermodynamics in designing a sustainable process," Design for Energy and the Environment - Proceedings of the Seventh International Conference on the Foundations of Computer-Aided Process Design, Eds., M. M. El-Halwagi and A. A. Linninger, CRC Press, Boca Raton, FL, pp. 233-241, 2010.

Zhang, X., R. Luo, Z. Wang, Y. Deng, and G. Chen, "Application of (R)-3-hydroxyalkanoate methyl esters derived from microbial polyhydroxyalkanoates as novel biofuels," Biomacromolecules, 10, 707-711, 2009.

Chen, K. S., and E. E. Kalu, "Final report on LDRD project: Biodiesel production from vegetable oils using slit-channel reactors," Sandia report, SAND2008-0213, 2008

Ehimen, E. A., "Energy Balance of Microalgal-derived Biodiesel," Energy Sources, Par A: Recovery, Utilization, and Environmental Effects, 32, 1111-1120, 2010

Lawford, H. G., and J. D. Rousseau, "Studies on nutrient requirements and cost-effective supplements for ethanol production by recombinant *E. coli*," Applied biochemistry and biotechnology, 57/58, 307-326

Madigan, M. T., J. M. Martinko, J. Parker, Brock Biology of Microorganisms, Prentice Hall, 12th Edition, 2009

Nagpal, S., S. Chuichulcherm, A. Livingston, and L. Peeva, "Ethanol utilization by sulfate-reducing bacteria: an experimental and modeling study," Biotechnology and Bioengineering, 70, 533-543, 2000

Lardon, L., A. Helias, B. Sialve, J. Steyer, and O. Bernard, "Life-cycle assessment of biodiesel production from microalgae," Policy Analysis, 43, 6475-6481, 2009

Shieh, J. H. and L. T. Fan, "Estimation of Energy (Enthalpy) and Exergy (Availability) Contents in Structurally Complicated Materials," Energy Sources, 6, 1 46 (1982)

International Application Number PCT/US2010/043392; International Search Report dated Sep. 21, 2010

International Application Number PCT/US2010/043392; Written Opinion of the International Searching Authority dated Sep. 21, 2010

U.S. Provisional Application No. 61/228,898 filed Jul. 27, 2009

U.S. Provisional Application No. 61/358,700 filed Jun. 25, 2010

Intentionally left blank

White Paper: Transitioning From First Generation to Advanced Biofuels; Enterprise Florida and GTM Research, February 2010, 15 pp.

Suzuki, I. and Werkman, C. H.; "Chemautotropic Carbon Dioxide Fixation by Extracts of *Thiobacillus* Thiooxidans I. Formation of Oxalacetic Acid, Iowa State College, 1957 Oct. 16; 9 pp.

U.S. Nonprovisional application No. 12/613,550, filed Nov. 6, 2009, entire file wrapper available on USPTO PAIR system U.S. Nonprovisional application No. 12/613,550 filed Nov. 6, 2009, Office Action dated Jun. 6, 2013

U.S. Provisional application No. 61/111,794, filed Nov. 6, 2008

U.S. Provisional application No. 61/782,762 Filed Mar. 14, 2013 "Systems and Methods for Conversion of Carbon Dioxide Utilizing Chemoautotrophic Microorganisms"

Patent application No. 13/127,697, filed May 4, 2011; entire file wrapper available on USPTO PAIR system Kuenen, J. G. and Bos, P; "Habits and Ecological Niches of Chemolitho(auto)trophic Bacteria," Autotrophic Bacteria, Brock/Springer Series in Contemporary Bioscience, Delft University of Technology; pp 53-59

Madigan, Michael T, et al; Brock Biology of Microorganisms, 5.6 Oxidation-Reduction pp 566-567

Maier, Raina M. et al; Environmental Microbiology; 2.2 Bacteria, p 27

Prescott Harley Klein, Microbiology, Sixth Edition, Chapter 5, Microbial Nutrition p 96; Chapter 8 Oxidation-Reduction Reactions and Electron Carriers, p 153; Chapter 9 Metabolism: Energy Release and Conservation, p 188; Glossary p G-5 vanLoon, W and Duffy, S; Environmental Chemistry, a global perspective; Second

-continued

Edition; Chapter 11.2 Gases that React with Water; p 241
Trudinger, PA; Fixation of Carbon Dioxide by Extracts of the Strict Autotroph *Thiobacillus denitrificans*"" Biochemical Journal, 64, 274-286, 1956
Taylor, James; Parkes, John; "The Cellular Fatty Acids of the Sulphate-reducing Bacteria *Desulfobacter* sp., *Desulfobulbus* sp. and *Desulfovibvio desulfuvicans*" Journal of General Microbiology, 129, 3303-3309, 1983
Lynd, Lee R; et al; "Fuel Ethanol from Cellulosic Biomass" Science, 251, 1318-1323, 1991

Thus, the applicant(s) should be understood to have support to claim and make a statement of invention to at least: i) each of the biological conversion devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC*, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:
1. A method of biologically reducing carbon dioxide pollutants comprising the steps of:
 containing at least some carbon dioxide emissions from a carbon dioxide emitter;
 introducing at least some carbon dioxide emissions from said carbon dioxide emitter into at least one processing reactor;

chemoautotrophically digesting carbon dioxide of said at least some carbon dioxide emissions with a plurality of chemoautotrophic bacteria in said at least one processing reactor;
providing a nitrogenous compound energy supply to said plurality of chemoautotrophic bacteria in said at least one processing reactor;
biologically producing at least some biomass from said chemoautotrophic digestion of said carbon dioxide with said chemoautotrophic bacteria;
providing a plurality of nitrate reducing bacteria in at least one additional processing reactor;
generating nitrite in said at least one additional processing reactor containing said plurality of nitrate reducing bacteria;
supplying said nitrite from said at least one additional processing reactor containing said plurality of nitrate reducing bacteria to said at least one processing reactor with said plurality of chemoautotrophic bacteria;
providing an acetate conversion reactor;
feeding acetate generated from said nitrate reducing bacteria into said acetate conversion reactor;
generating biomass from said acetate conversion reactor; and
ecologically reducing atmospheric release of said carbon dioxide emitted from said carbon dioxide emitter.

2. A method of biologically reducing carbon dioxide pollutants according to claim 1 wherein said step of containing said at least some carbon dioxide emissions from said carbon dioxide emitter comprises the step of containing up to about 100% of said at least some carbon dioxide emissions from said carbon dioxide emitter.

3. A method of biologically reducing carbon dioxide pollutants according to claim 1 wherein said industrial carbon dioxide emitter is selected from a group consisting of power generation sources, mining operations, municipal waste landfills, cement producing plants, lime producing plants, coal refineries, oil refineries, refineries, trona processing plants, Fischer-Tropsch synthesis plants, coal-to-liquids plants, gas-to-liquids plants, biomss-to-liquids plants, gasification facilities, non-power generation sources, coal-fired power plants, natural gas-fired power plants, fuel cells, and combustion power plants.

4. A method of biologically reducing carbon dioxide pollutants according to claim 1 wherein said chemoautotrophic bacteria are selected from a group consisting of the genera *Nitrosomonas, Nitrosococcus, Nitrosospira, Nitrosolobus, Pedobacter, Nitrobacter, Nitrococcus, Nitrospina*, any bacteria that naturally nitrifies, and combinations thereof.

5. A method of biologically reducing carbon dioxide pollutants according to claim 1 wherein said chemoautotrophic bacteria comprises genetically engineered chemoautotrophic bacteria for nitrification.

6. A method of biologically reducing carbon dioxide pollutants according to claim 1 and further comprising the steps of:
generating nitrate in said at least one processing reactor containing said chemoautotrophic bacteria;
supplying said nitrate from said at least one processing reactor containing said chemoautotrophic bacteria to said at least one additional processing reactor containing said nitrate reducing bacteria;
generating ammonia or ammonium in said at least one additional processing reactor containing said nitrate reducing bacteria; and
supplying said ammonia or ammonium from said at least one additional processing reactor containing said nitrate reducing bacteria to said at least one processing reactor containing said plurality of chemoautotrophic bacteria.

7. A method of biologically reducing carbon dioxide pollutants according to claim 1 and further comprising the steps of:
generating an element selected from a group consisting of nitrate, nitrite, and a combination thereof in said at least one processing reactor containing said chemoautotrophic bacteria;
supplying said element from said at least one processing reactor containing said chemoautotrophic bacteria to said at least one additional processing reactor containing said nitrate reducing bacteria;
generating nitrogen gas in said at least one additional processing reactor containing said nitrate reducing bacteria;
reacting said nitrogen produced in said at least one additional processing reactor in a chemical process to produce ammonia; and
supplying said ammonia from said chemical process to said at least one processing reactor containing said plurality of chemoautotrophic bacteria.

8. A method of biologically reducing carbon dioxide pollutants according to claim 1 and further comprising the steps of:
supplying an ammonia element selected from a group consisting of ammonia, ammonium, ammonia nitrate, and any combination thereof to said at least one processing reactor containing said plurality of chemoautotrophic bacteria;
generating an element selected from a group consisting of nitrate, nitrite, or a combination thereof in said at least one processing reactor containing said plurality of chemoautotrophic bacteria;
supplying said element from said at least one processing reactor containing said plurality of chemoautotrophic bacteria to said at least one additional processing reactor containing said nitrate reducing bacteria;
producing nitrogen in said at least one additional processing reactor containing said plurality of nitrate reducing bacteria; and
releasing said produced nitrogen.

9. A method of biologically reducing carbon dioxide pollutants according to claim 8 and further comprising the step of providing recycled process biomass residue as an electron donor supply to said nitrate reducing bacteria.

10. A method of biologically reducing carbon dioxide pollutants according to claim 1 and further comprising the steps of:
connecting said at least one processing reactor containing said plurality of chemoautotrophic bacteria to said at least one additional processing reactor containing said plurality of nitrate reducing bacteria;
generating nitrate in said at least one processing reactor containing said chemoautotrophic bacteria; and
supplying said nitrate from said at least one processing reactor containing said plurality of chemoautotrophic bacteria to said at least one additional processing reactor containing said plurality of nitrate reducing bacteria.

11. A method of biologically reducing carbon dioxide pollutants according to claim 1 and further comprising the steps of:
generating an element selected from a group consisting of nitrate, nitrite, or a combination thereof in said at least one processing reactor containing said plurality of chemoautotrophic bacteria;

supplying said element from said at least one processing reactor containing said plurality of chemoautotrophic bacteria to said at least one additional processing reactor containing said nitrate reducing bacteria;

producing nitrogen in said at least one additional processing reactor containing said plurality of nitrate reducing bacteria; and releasing said produced nitrogen.

* * * * *